United States Patent
Guo et al.

(10) Patent No.: US 12,220,118 B2
(45) Date of Patent: Feb. 11, 2025

(54) SYSTEMS, DEVICES AND METHODS FOR RECONSTITUTING THERAPEUTIC POWDERS, MIXING PRECURSOR SOLUTIONS, AND EXPRESSING SEALANTS FOR CONTROLLING BLEEDING AND SEALING FLUID AND AIR LEAKS

(71) Applicant: Ethicon, Inc., Somerville, NJ (US)

(72) Inventors: Jianxin Guo, Livingston, NJ (US);
Sridevi N. Dhanaraj, Raritan, NJ (US);
Salim Ghodbane, Piscataway, NJ (US)

(73) Assignee: Ethicon, Inc., Somerville, NJ (US)

( * ) Notice: Subject to any disclaimer, the term of this patent is extended or adjusted under 35 U.S.C. 154(b) by 455 days.

(21) Appl. No.: 17/710,094

(22) Filed: Mar. 31, 2022

(65) Prior Publication Data
US 2023/0309977 A1    Oct. 5, 2023

(51) Int. Cl.
*A61B 17/00* (2006.01)
*A61M 5/19* (2006.01)
(Continued)

(52) U.S. Cl.
CPC ......... *A61B 17/00491* (2013.01); *A61M 5/19* (2013.01); *A61M 5/2429* (2013.01);
(Continued)

(58) Field of Classification Search
CPC ... A61B 17/00491; A61B 2017/00495; A61M 5/19; A61M 5/2429; A61M 5/2448; A61M 5/3137; A61M 5/31596
(Continued)

(56) References Cited

U.S. PATENT DOCUMENTS

| 3,563,373 A | 2/1971 | Paulson |
| 3,923,058 A | 12/1975 | Weingarten |

(Continued)

FOREIGN PATENT DOCUMENTS

| CN | 102911493 A | 2/2013 |
| CN | 104159626 A | 11/2014 |

(Continued)

OTHER PUBLICATIONS

The Confidence to Know Bleeding Will Stop. Veriset Hemostatic Patch, https://www.medtronic.com/content/dam/covidien/library/emea/en/product/haemostatic-products/weu-veriset-or-guide-lap-open-combined.pdf, 2021, 2 pages, Medtronic.
(Continued)

*Primary Examiner* — Kevin T Truong
*Assistant Examiner* — Diana Jones
(74) *Attorney, Agent, or Firm* — Troutman Pepper Locke LLP

(57) ABSTRACT

A sealant delivery system includes a syringe assembly having side-by-side syringes and a vial assembly having side-by-side vials. A first vial is aligned with a distal end of a first syringe and has a vial opening at the proximal end thereof that is closed by a first sealing membrane. A second vial is aligned with a distal end of a second syringe and has a second vial opening at the proximal end thereof that is closed by a second sealing membrane. The vial assembly includes a first piercing element moveable between a retracted position and an extended position for piercing the first sealing membrane to provide fluid communication between the first fluid chamber and the first vial, and a second piercing element moveable between a retracted position and an extended position for piercing the second sealing membrane to provide fluid communication between the second fluid chamber and the second vial.

12 Claims, 21 Drawing Sheets

(51) Int. Cl.
*A61M 5/24* (2006.01)
*A61M 5/31* (2006.01)
*A61M 5/315* (2006.01)

(52) U.S. Cl.
CPC ........ *A61M 5/2448* (2013.01); *A61M 5/3137* (2013.01); *A61M 5/31596* (2013.01); *A61B 2017/00495* (2013.01)

(58) Field of Classification Search
USPC ........................................................... 606/88
See application file for complete search history.

(56) References Cited

U.S. PATENT DOCUMENTS

| | | | |
|---|---|---|---|
| 4,059,109 A | 11/1977 | Tischlinger | |
| 4,060,082 A | 11/1977 | Lindberg et al. | |
| 4,424,057 A | 1/1984 | House | |
| 4,631,055 A | 12/1986 | Redl et al. | |
| 4,723,691 A | 2/1988 | Minkevitch et al. | |
| 5,304,165 A * | 4/1994 | Haber .................. | A61J 1/2096 604/411 |
| 6,224,568 B1 | 5/2001 | Morimoto et al. | |
| 6,458,095 B1 | 10/2002 | Wirt et al. | |
| 6,471,670 B1 | 10/2002 | Enrenfels et al. | |
| 6,475,183 B1 | 11/2002 | Epstein et al. | |
| 6,488,650 B1 | 12/2002 | Epstein et al. | |
| 6,569,113 B2 | 5/2003 | Wirt et al. | |
| 6,575,205 B2 | 6/2003 | Epstein et al. | |
| 6,605,667 B1 | 8/2003 | Badejo et al. | |
| 6,610,033 B1 | 8/2003 | Melanson et al. | |
| 6,699,229 B2 | 3/2004 | Zinger et al. | |
| 7,037,289 B2 | 5/2006 | Dodge et al. | |
| 7,081,103 B2 | 7/2006 | Epstein et al. | |
| 7,021,561 B2 | 8/2006 | Vedrine et al. | |
| 7,207,969 B2 | 4/2007 | Epstein et al. | |
| 7,322,956 B2 | 1/2008 | Fehr et al. | |
| 7,923,031 B2 | 4/2011 | Moller | |
| 7,946,417 B2 | 5/2011 | Plishka et al. | |
| 7,951,108 B2 | 5/2011 | Harper et al. | |
| 7,967,779 B2 | 6/2011 | Bertron et al. | |
| 8,029,468 B2 | 10/2011 | Kriesel et al. | |
| 8,323,262 B2 | 12/2012 | D'Alessio et al. | |
| 8,419,722 B2 | 4/2013 | Richards et al. | |
| 8,821,436 B2 | 9/2014 | Mosler et al. | |
| 9,131,930 B2 | 9/2015 | Greter | |
| 9,398,913 B2 | 7/2016 | Tegels et al. | |
| 9,539,393 B2 | 1/2017 | Johannesson et al. | |
| 9,717,487 B2 | 8/2017 | White et al. | |
| 9,873,098 B2 * | 1/2018 | Asada .................. | B01F 35/7174 |
| 10,183,132 B2 | 1/2019 | Wang et al. | |
| 10,420,888 B2 | 9/2019 | Arocha | |
| 10,507,293 B2 | 12/2019 | Goodman et al. | |
| D921,189 S | 6/2021 | Shor et al. | |
| 2001/0016709 A1 | 8/2001 | Tovey et al. | |
| 2003/0040701 A1 | 2/2003 | Dalmose | |
| 2003/0225378 A1 | 12/2003 | Wilkie et al. | |
| 2006/0079834 A1 * | 4/2006 | Tennican ............... | A61M 5/204 206/363 |
| 2009/0209916 A1 | 8/2009 | Peindl et al. | |
| 2010/0219200 A1 | 9/2010 | Plishka et al. | |
| 2011/0178495 A1 | 7/2011 | Ji | |
| 2013/0296822 A1 * | 11/2013 | Yokoyama ............... | A61J 1/16 604/413 |
| 2013/0324884 A1 | 12/2013 | Hadvary et al. | |
| 2013/0331658 A1 | 12/2013 | Kai et al. | |
| 2013/0338631 A1 * | 12/2013 | Butlin ..................... | A61M 5/19 604/506 |
| 2014/0114211 A1 | 4/2014 | Hadvary et al. | |
| 2016/0015900 A1 | 1/2016 | Cronenberg et al. | |
| 2018/0110927 A1 | 4/2018 | Frias Goyenechea et al. | |
| 2018/0117261 A1 | 5/2018 | Steese-Bradley et al. | |
| 2019/0151546 A1 | 5/2019 | Maloney et al. | |
| 2019/0217010 A1 | 7/2019 | Dungar et al. | |
| 2019/0269818 A1 | 9/2019 | Dhanaraj et al. | |
| 2019/0321554 A1 | 10/2019 | Guo et al. | |
| 2020/0360004 A1 | 11/2020 | Guo et al. | |
| 2021/0101162 A1 | 4/2021 | Trezza, II et al. | |
| 2021/0162122 A1 | 6/2021 | Pic et al. | |
| 2022/0133287 A1 | 5/2022 | Addison et al. | |
| 2023/0309978 A1 | 10/2023 | Guo et al. | |

FOREIGN PATENT DOCUMENTS

| | | |
|---|---|---|
| CN | 105194771 A1 | 12/2015 |
| CN | 108159483 A | 6/2018 |
| CN | 112334077 A | 2/2021 |
| CN | 113521376 A | 10/2021 |
| CN | 113631100 A | 11/2021 |
| EP | 0188981 | 7/1986 |
| EP | 0292472 | 10/1991 |
| EP | 1656214 | 2/2010 |
| EP | 2944277 A1 | 11/2015 |
| JP | 2019171107 | 10/2019 |
| WO | 2001049361 A1 | 7/2001 |
| WO | 2009153042 | 12/2009 |
| WO | 2010134988 A1 | 11/2010 |
| WO | 2012158973 | 11/2012 |
| WO | 2013063396 A1 | 5/2013 |
| WO | 2013134614 A3 | 10/2013 |
| WO | 2016038593 A1 | 3/2016 |
| WO | 2016160469 | 10/2016 |
| WO | 2016038593 A8 | 4/2017 |
| WO | 2018150375 | 8/2018 |
| WO | 2019018198 | 1/2019 |
| WO | 2019077381 | 4/2019 |
| WO | 2019202446 A1 | 10/2019 |
| WO | 2019237080 | 12/2019 |
| WO | 2020197969 A1 | 10/2020 |
| WO | 2021250548 A1 | 12/2021 |
| WO | 2022038439 A1 | 2/2022 |

OTHER PUBLICATIONS

Search Report (English translation) dated Nov. 1, 2023, from corresponding Chinese Patent Application No. 202210756477.7.
Search Report (English translation) dated Nov. 3, 2023, from corresponding Chinese Patent Application No. 202211660674.5.
International Search Report and Written Opinion dated Jun. 20, 2023, from corresponding International Patent Application No. PCT/IB2023/052537.
International Search Report and Written Opinion dated Jun. 14, 2023, from corresponding International Patent Application No. PCT/IB2023/052516.

* cited by examiner

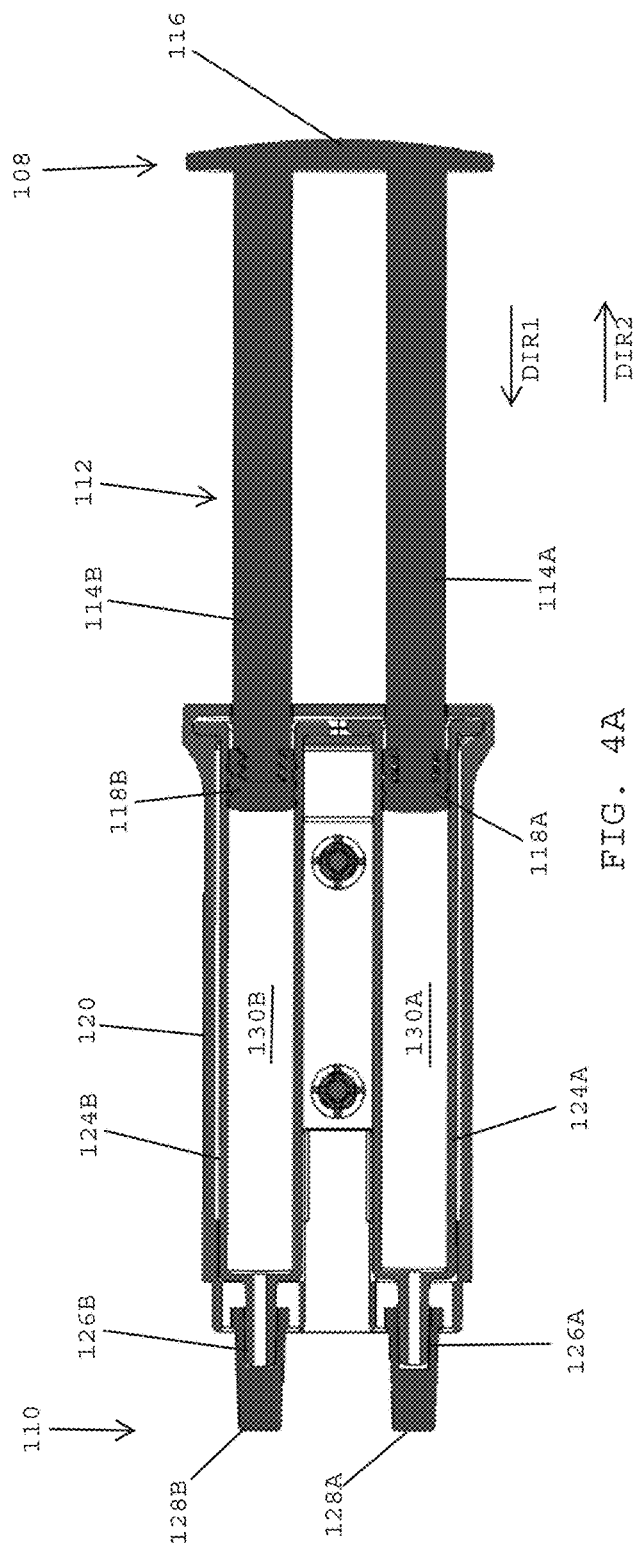
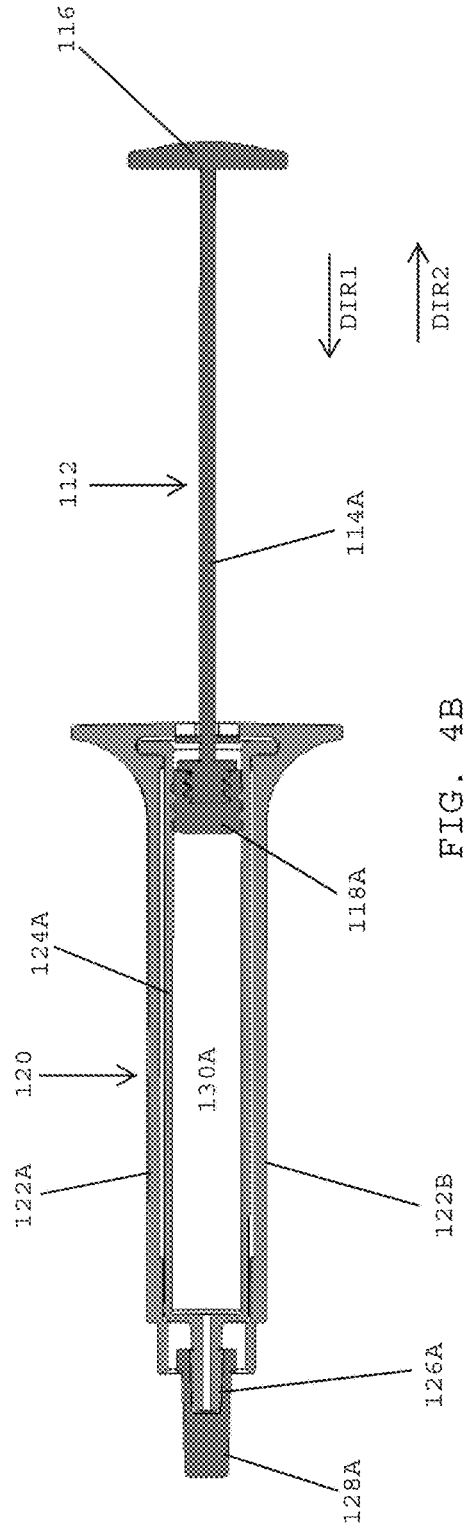
FIG. 4A
FIG. 4B

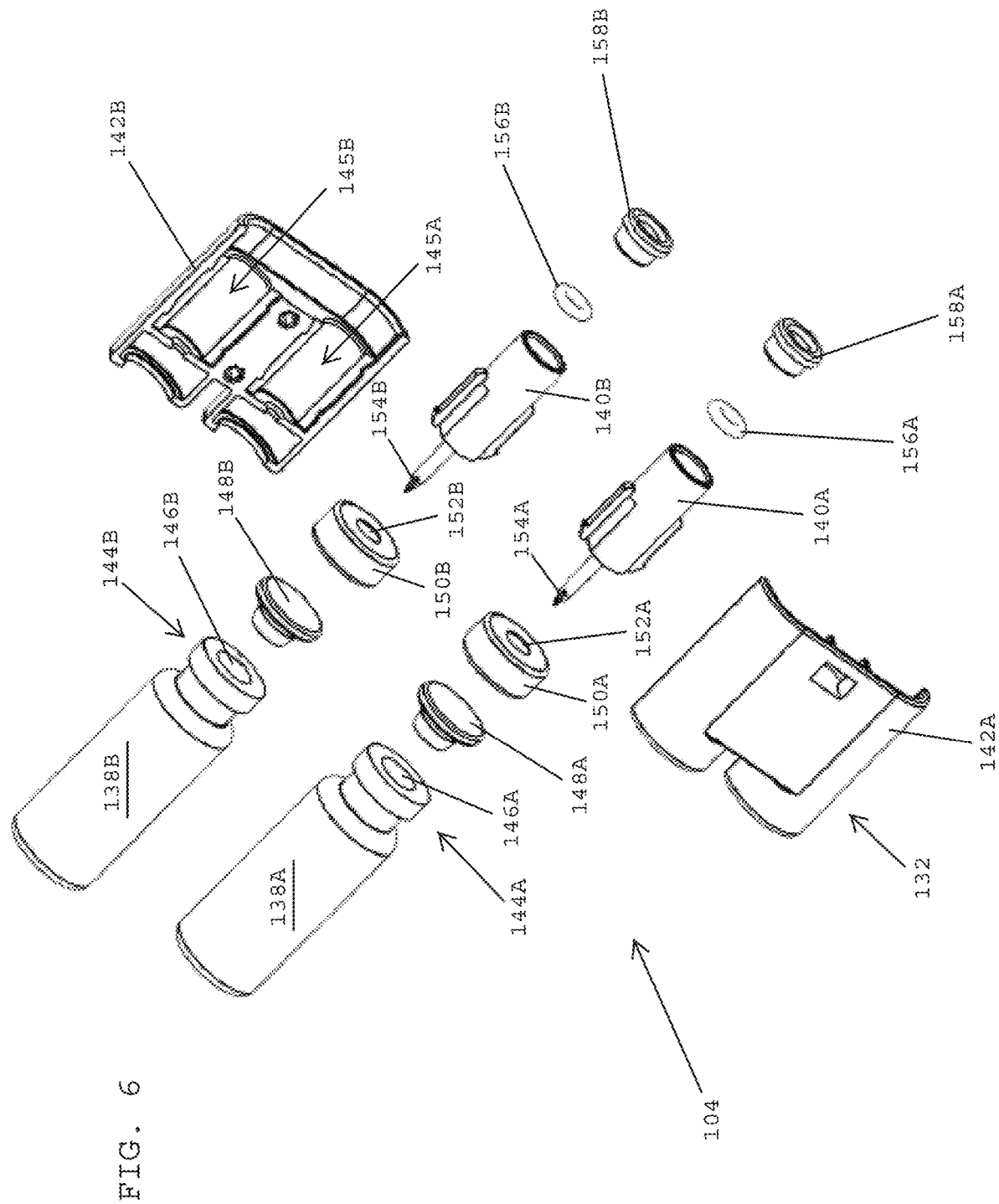

SYSTEMS, DEVICES AND METHODS FOR RECONSTITUTING THERAPEUTIC POWDERS, MIXING PRECURSOR SOLUTIONS, AND EXPRESSING SEALANTS FOR CONTROLLING BLEEDING AND SEALING FLUID AND AIR LEAKS

BACKGROUND OF THE INVENTION

Field of the Invention

The present patent application is generally related to systems, devices and methods for dispensing therapeutic fluids during surgical procedures, and is more specifically related to system, devices and methods for dispensing therapeutic fluids that are used for controlling bleeding, sealing wounds, sealing air leaks during lung surgery, sealing fluid leaks, and graft fixation.

Description of the Related Art

In a wide variety of circumstances, mammals can suffer from bleeding due to wounds or during surgical procedures. In some instances, the bleeding is relatively minor and will stop due to normal blood clotting functions or by using simple first aid techniques. In other instances, however, substantial bleeding can occur. These latter instances require the use of specialized equipment and materials, as well as the services of trained personnel in order to administer effective aid to control excessive bleeding.

To address the more challenging circumstances noted above, various materials have been developed for controlling excessive bleeding. For example, topical absorbable hemostats (TAHs) are widely used in surgical applications. TAHs encompass products based on oxidized cellulose (OC), oxidized regenerated cellulose (ORC), gelatin, collagen, chitin, chitosan, starch, etc. To improve the hemostatic performance, scaffolds based on the above materials can be combined with biologically derived clotting factors, such as thrombin and fibrinogen.

Controlling bleeding is essential and critical in surgical procedures to minimize blood loss, shorten the duration of the surgery, and reduce post-surgical complications.

Recently, minimally invasive surgery (MIS) techniques (e.g., thoracic surgery) have emerged as an alternative to conventional surgical techniques for performing a wide range of surgical procedures. MIS procedures differ from conventional surgical procedures in that a plurality of devices and/or surgical tools may be introduced into the body through cannulas and/or trocars, which are inserted into small incisions made in the body. As a result of using MIS techniques, trauma to the body is greatly reduced, which decreases recovery time for patients.

One type of minimally invasive surgery involves laparoscopic surgical procedures, which are used to treat hernias, colon dysfunctions, gastroesophageal reflux disease, gallbladder disorders, lung disorders, etc. Typically, a patient undergoing a laparoscopic surgical procedure is able to return home after a short recovery period (e.g., within hours after undergoing surgery).

One challenge presented when performing MIS procedures relates to controlling bleeding at the surgical site. In contrast to conventional open surgical procedures; during a laparoscopic procedure a surgeon's access to a surgical site or surgical cavity is greatly reduced.

In response, tissue sealants and other biological adhesive materials have been developed for use in closing incisions and wounds at surgical sites. Tissue sealants may include fibrin sealants, which is composed of thrombin, and a fibrinogen material; although other formulations are also available. Typically, the individual components of the tissue sealants (e.g., thrombin and fibrinogen) are stored separately in isolated reservoirs because the components will rapidly react once they come in contact with one another. In many instances, the two separate components are mixed together for the first time immediately prior to being applied to tissue.

Once mixed, the components coagulate very quickly, yielding an adhesive gel within a short period of time (e.g., within 10-20 seconds).

There have been some developments related to systems for reconstituting therapeutic powders to form therapeutic solutions and delivering the therapeutic solutions to patients. For example, U.S. Pat. No. 4,723,691 discloses a hand-held and hand-operable powder dispenser having a container including a handle/nozzle section terminating at its discharge end in an unobstructed powder dispensing opening, a hand gripping section, and a central, flexible bellows section coupled between the handle/nozzle section and the hand-gripping section. The bellows section is adapted to be collapsed and expanded axially to serve as a pump. The inside diameters of the handle/nozzle section decrease substantially linearly and continually as a function of the length of the handle/nozzle section in a direction toward the powder dispensing opening.

US 2003/0040701 discloses a dual chamber syringe in which a dual function piston divides the syringe into two compartments containing powder or fluid in one compartment and fluid in the other. In order to mix the two substances, a passage is opened between the two compartments before or during retraction of the piston to force the substances to be mixed in the front compartment. During forward movement of the piston, the passage between the two compartments is closed to force the mixture of substances through the discharge opening of the syringe.

U.S. Pat. No. 6,458,095 discloses a dispenser for simultaneously dispensing first and second components of an adhesive tissue sealant, wherein at least the first component is stored in the dispenser as dry powder that is dissolved prior to use by introduction of a solvent. The dispenser includes a first container having a first septum at one end, an open end opposite the first septum, and a first movable plug disposed therein. The first container holds a quantity of the first component in the form of a dry powder stored between the first septum and the first movable plug. The dispenser includes a second container having a second septum at one end, an open end opposite the second septum, and a second movable plug disposed therein, the second container containing a quantity of the second component.

U.S. Pat. No. 6,699,229 discloses a fluid transfer and mixing device for use in the aseptic intermixing of a powder component with a fluid component. The device includes a first adapter that can be connected to a container holding the powder component and a second adapter that can be removably interconnected with the first adapter and can also be readily connected to a container containing a fluid, such as a diluent, to permit aseptic intermixing of the diluent with the powder. In use, a syringe is connected to the first adapter so that the mixture of the powder and the diluent can be aseptically aspirated from the first container for delivery to a patient.

US 2010/0219200 discloses an apparatus and method for mixing two components and delivering the mixture to a patient. The apparatus contains a mixing chamber for mixing a liquid component and a powder component. The liquid component and the powder component are mixed within the mixing chamber by rotation of a collapsible mixing element. A plunger is advanced through the mixing chamber to force the mixture out of the mixing chamber and deliver the mixture to a patient.

U.S. Pat. No. 7,923,031 discloses a powder delivery system including a chamber storing a hemostatic composition comprising dry gelatin powder having a mean particle size in the range of 30-250 micrometers and hyaluronic acid. The system includes a chamber having at least one discharge opening sized for distributing the composition.

U.S. Pat. No. 7,946,417 discloses an apparatus and method for mixing two components and delivering the mixture to a patient. The apparatus contains a mixing chamber for mixing a liquid component and a powder component. The liquid component and powder component are mixed within the mixing chamber by rotation of a collapsible mixing element. A plunger is then advanced through the mixing chamber to force the mixture out of the mixing chamber and deliver the mixture to the patient.

US 2011/0178495 discloses a powder supply device that includes a gas powder mixer providing a gas powder mixing chamber and a powder dispenser (bellows) which is screwed to the gas powder mixer and communicated with the gas powder mixing chamber therein. The hemostat powder is filled in the powder dispenser (bellows) and is adapted to be delivered via the powder delivery catheter to the site of bleeding.

U.S. Pat. No. 7,967,779 discloses a mixing syringe having a first sealed chamber containing a powder (powder housing) and a second sealed chamber containing a liquid (liquid housing). When the user needs to inject a patient, the device is held approximately upright while depressing a plunger, which causes a piercing element to pierce a foil seal separating the two chambers. Liquid then drops down into the powder housing. The liquid flows through a passage in a piston located in the powder housing, where it contacts the powder. As the user continues pressing the plunger downward, the piercer comes to rest within the piston and seals the passage through the piston, thereby locking the piercer and piston together. The device is then ready for an injection. As the plunger is further depressed, the piston expels the powder and liquid mixture through a needle.

U.S. Pat. No. 10,183,132, assigned to Ethicon LLC, the disclosure of which is hereby incorporated by reference herein, teaches an integrated delivery device that is operable with one hand and provides co-delivery of a liquid medicant and a powder medicant onto a tissue or wound from a liquid medicant expression subunit and a powder medicant expression subunit. Each expression subunit has an actuator for the liquid medicant and the powder medicant contained therein, which are positioned near one other at proximal ends of the expression subunits and delivery cannulas for each of the said expression subunits that positioned near one other at distal ends of the expression subunits.

U.S. Pat. No. 10,507,293 to Goodman et al., assigned to Ethicon, Inc. of Somerville, New Jersey, the disclosure of which is hereby incorporated by reference herein, teaches a device for the expression of a hemostatic powder. The device has an elongated reservoir with a manual air pump, such as a bellows, at a proximal end and an expression port at a distal end. A porous filter is slidably disposed within the reservoir between the bellows and plunger and the expression port, and a spring is disposed within the reservoir between the air pump and the plunger. The powder is disposed within the reservoir between the porous filter and the expression port, and the pump is in a fluid communication with the expression port through the porous filter and through the powder.

US 2021/0101162, assigned to Ethicon, Inc., the disclosure of which is hereby incorporated by reference herein, discloses a spray device including a first spray tip having a first fluid pathway defining a first flow area, and a second spray tip includes a second fluid pathway that defines a second flow area that is larger than the first flow area of the first spray tip. The first and second spray tips are side-by-side and spaced from one another at a distal end of the spray device. When a first fluid having a volumetric flow rate is introduced into the first spray tip and a second fluid having the same volumetric flow rate is introduced into the second spray tip, the first fluid will flow through the first fluid pathway at a greater velocity than the second fluid will flow through the second fluid pathway.

There have been some efforts directed to controlling intra and post-operative bleeding, fluid leaks, and air leaks that occur during thoracic surgery, such as during the resection of an organ.

A resection is a surgical procedure that involves cutting out tissue or a part of an organ. Resections, which are performed on a wide variety of organs including livers, lungs and gastrointestinal systems, present surgeons with many unique problems related to effectively managing post-operative bleeding, and fluid and air leaks.

During organ resection procedures, surgeons manage major bleeding at resected surfaces by using tourniquets, extensive suturing, etc. Some surgeons use adhesive fluids (e.g., synthetic adhesives, fibrin glue gels), which are limited since they can flow off the resected surface prior to completely curing or can peel off easy following curing since they lack adequate adherence to underlying tissue or proper elastic properties.

Liver Resection. A surgical procedure that involves removing all or part of a liver is commonly referred to as a hepatectomy. A partial hepatectomy is a preferred approach for removing a solid tumor from a liver. During resection of a liver, the tissue margins within the resected area are destroyed and the internal parenchyma and flow systems are exposed. The re-establishment of proper margins does not occur immediately, but requires an extended tissue healing process that can last from days to weeks. During the tissue healing process, the resected tissue can ooze blood and/or leak organ specific liquids (e.g., bile), which can cause post-operative complications. One study found that after liver resection procedures, the bile leakage rate was about 5%, which dramatically increased the likelihood of patient post-operative complications.

Lung Resection. Lung resection procedures typically require a significant amount of tissue manipulation and handling, which results in a high incidence of post operative air leaks. Standardized techniques that are used to address air leaks involve suturing or stapling the lung tissue. These techniques are often ineffective, however, in creating an airtight seal due to the intrinsic friability of the lung parenchyma, particularly in emphysematous patients. In some instances, topical adhesives are applied either directly on the pleural abrasion or onto staple lines, however, these techniques are often inadequate for preventing air leaks.

GI Resection. Gastrointestinal (GI) procedures often involve excising large segments of a patients intestinal anatomy for effectively treating disease. After removing GI tissue, surgeons are required to reconstruct the patients digestive system. GI reconstructions are complicated due to the delicate structure of the intestines, limited blood supply to lower colon, limited surgeon access to complex anatomical structures, and the pathologies that typically affect the surrounding tissues. Even when surgeons exercise great care during GI reconstruction procedures, however, there are a certain percentage of patients who will have complications resulting from leaks at surgically created anastomotic sites, GI leaks can result in devastating outcomes, requiring additional surgeries and treatments that are often unsuccessful in managing the leaks.

In view of the above, there have been many efforts directed to effectively managing intra and post-operative bleeding, and fluid and air leaks. For example, when resecting solid organs, surgeons typically manage major bleeding at resected surfaces by using tourniquets and extensive suturing. Minor bleeding and fluid leakage is often managed by using adhesive fluids (e.g., synthetic adhesives, fibrin glue) to cover the resected surfaces, however, these methodologies have achieved limited success because the adhesive fluids tend to flow off of the resected surfaces prior to curing and/or peel off after curing because the cured adhesive lacks adequate adherence to underlying tissue or proper elastic properties.

Covidien sells a VERISET® hemostatic patch for sealing resected tissue surfaces. The VERISET® hemostatic patch is composed of an oxidized regenerated cellulose (ORC) layer and a reactive polyethylene glycol (PEG) layer. The patch is applied to a tissue surface by applying pressure on the surface. Due to the fact that the OR® matrix is opaque, while applying pressure onto the resected surface, a surgeon cannot see through the VERISET® hemostatic patch to assess the condition of the resected surface. The patch is also rigid with low flexibility and therefore may not achieve good tissue conformability or remain compliant with tissue movements.

In spite of the above-identified developments, there is a continuing need for improved systems, devices and methods that enable surgeons to effectively seal surfaces of organs and tissue, and to prevent and/or successfully manage intra and post-operative bleeding, fluid leaks and/or air leaks from surfaces (e.g., resected surfaces) of organs and tissue.

SUMMARY OF THE INVENTION

In one embodiment, a sealant applicator system for mixing and delivering sealants or hemostats during a surgical procedure preferably includes two syringes for mixing and reconstituting powdered reactive components. In one embodiment, the two syringes are preferably held side-by-side by a syringe holder.

In one embodiment, the syringe holder may be formed by joining two syringe holder parts, each syringe holder part having two hollow cavities that are configured to accommodate at least a portion of the two syringes.

In one embodiment, each syringes contains a liquid (e.g., a diluent; a buffer solution; a catalyst; an initiator: an activation fluid, etc.) that may be mixed with a powdered reactive component for reconstituting the powdered reactive component.

In one embodiment, the sealant applicator system preferably includes two vials, each vial being configured for holding a powdered reactive component. In one embodiment, each vial is closed by a pierceable sealing membrane (e.g., a septum; a stopper) that seals a vial opening for maintaining the powdered reactive component in a dry state during shipment and storage.

In one embodiment, the two vials are held side-by-side in a vial holder. In one embodiment, the vial holder includes two piercing elements, each piercing element having a proximal end with a central opening or hub, and a distal end having a spike, each spike having a sharp point that can pierce one of the sealing membranes. In one embodiment, the piercing elements are held side-by-side within the vial holder, with the sharp points of the spikes pointing toward the sealing membranes.

In one embodiment, the vial holder may be formed by joining two vial holder parts, each vial holder part having two hollow cavities that are configured to accommodate at least a portion of the vials and the piercing elements.

In one embodiment, the side-by-side piercing elements are slidably movable in the vial holder, with the sharp points of the spikes configured to pierce the sealing membranes when moved toward the sealing membranes.

In one embodiment, the proximal end of each piercing element preferably includes a port that is connectible to a distal end of one of the syringes. Each piercing element preferably has an elongated conduit that extends along the length of the piercing element, between the port at the proximal end and the sharp point at the distal end of the piercing element.

In one embodiment, the piercing elements have proximal ends that are coupled with the distal ends of the syringes for establishing fluid communication between the syringes and the respective vials.

In one embodiment, the sealant applicator system may include an elongated expression tip with a mixing tip at a distal end and a housing at a proximal end adapted for connection to said syringes.

In one embodiment, the elongated expression tip may include a cannula with two lumens for conveying two components of the sealant from the syringes toward a mixing tip.

In one embodiment, the elongated expression tip is bendable at the distal end. In one embodiment, the bendable portion of the elongated expression tip may include a malleable component having shape memory properties for maintaining the orientation of the mixing tip after the distal end of the elongated expression tip has been bent into a particular shape.

In one embodiment, the sealant applicator system may include a single piece syringe housing having side-by-side double barrel cavities for holding the liquids that are used for reconstitution and mixing.

In one embodiment, a sealant delivery system preferably includes a syringe assembly including side-by-side first and second syringes, the first syringe having a first fluid chamber and the second syringe having a second fluid chamber.

In one embodiment, the sealant delivery system preferably includes a vial assembly coupled to a distal end of the syringe assembly, the vial assembly including side-by-side first and second vials.

In one embodiment, the vial assembly and the syringe assembly preferably have structural features, which ensure that the first syringe may only be coupled with the first vial and the second syringe may only be coupled with the second vial. Thus, the design of the vial assembly and the syringe assembly desirably ensures that the first syringe always matches with the first vial and the second syringe always matches with the second vial. In one embodiment, if medical personnel attempt to couple the first syringe with the second vial and the second syringe with the first vial, the structural features of the syringe assembly and the vial assembly will prevent the distal end of the syringe assembly from being connected with the proximal end of the vial assembly.

In one embodiment, the first vial has a proximal end that is aligned with a distal end of the first syringe.

In one embodiment, the first vial includes a first vial opening at the proximal end thereof that is closed by a first sealing membrane.

In one embodiment, the second vial has a proximal end that is aligned with a distal end of the second syringe.

In one embodiment, the second vial includes a second vial opening at the proximal end thereof that is closed by a second sealing membrane.

In one embodiment, the vial assembly preferably includes a first piercing element located between the distal end of the first syringe and the proximal end of the first vial. The first piercing element may have a first piercing spike projecting from a distal end thereof.

In one embodiment, the first piercing element is moveable between a retracted position in which the first piercing spike is located on a proximal side of the first sealing membrane and an extended position in which the first piercing spike passes through the first sealing element for piercing the first sealing membrane to provide fluid communication between the first fluid chamber of the first syringe and the first vial.

In one embodiment, the vial assembly includes a second piercing element located between the distal end of the second syringe and the proximal end of the second vial. The second piercing element may have a second piercing spike projecting from a distal end thereof.

In one embodiment, the second piercing element is moveable between a retracted position in which the second piercing spike is located on a proximal side of the second sealing membrane and an extended position in which the second piercing spike passes through the second sealing element for piercing the second sealing membrane to provide fluid communication between the second fluid chamber of the second syringe and the second vial.

In one embodiment, the first piercing element defines a first fluid pathway extending along the length thereof for providing first fluid communication between the first fluid chamber of the first syringe and the first vial.

In one embodiment, the second piercing element defines a second fluid pathway extending along the length thereof for providing second fluid communication between the second fluid chamber of the second syringe and the second vial.

In one embodiment, the first and second fluid pathways are isolated from one another.

In one embodiment, a first liquid may be disposed within the first fluid chamber of the first syringe, and a first powdered reactive component may be disposed within the first vial. In one embodiment, the first liquid and the first powdered reactive component are configured for being mixed together for reconstituting the first powdered reactive component to form a first solution (e.g., a first precursor; a first therapeutic solution, etc.).

In one embodiment, a second liquid may be disposed within the second fluid chamber of the second syringe, and a second powdered reactive component may be disposed within the second vial. In one embodiment, the second liquid and the second powdered reactive component are configured for being mixed together for reconstituting the second powdered reactive component to form a second solution (e.g., a second precursor; a second therapeutic solution, etc.).

In one embodiment, the vial assembly housing may include a first guide channel (e.g., a cavity) extending between a proximal end and a distal end of the vial assembly housing. In one embodiment, the first piercing element is disposed in the first guide channel and is configured for moving (e.g., sliding) between the retracted position and the extended position.

In one embodiment, the vial assembly housing may include a second guide channel (e.g., a cavity) extending between the proximal end and the distal end of the vial assembly housing. In one embodiment, the second piercing element is disposed in the second guide channel and is configured for moving (e.g., sliding) between the retracted position and the extended position.

In one embodiment, the vial assembly housing may include a first proximal projection extending into the first guide channel that is adapted to contact the first piercing element for holding the first piercing element in the retracted position, and a first distal projection extending into the first guide channel that is adapted to contact the first piercing element for holding the first piercing element in the extended position. Thus, in one embodiment, the first piercing element may be secured (e.g., locked) in either the retracted position or the extended position.

In one embodiment, the vial assembly housing may include a second proximal projection extending into the second guide channel that is adapted to contact the second piercing element for holding the second piercing element in the retracted position, and a second distal projection extending into the first guide channel that is adapted to contact the first piercing element for holding the first piercing element in the extended position. Thus, in one embodiment, the second piercing element may be secured (e.g., locked) in either the retracted position or the extended position.

In one embodiment, the first piercing element may include a first resilient flange adapted to sequentially engage the first proximal projection and the first distal projection of the vial assembly housing when moving the first piercing element within the first guide channel from the retracted position to the extended position. When a force is applied to the proximal end of the first piercing element to slide the first piercing element toward the distal end of the vial housing, the first resilient element may flex for enabling the first piercing element to slide from the retracted position to the extended position. In one embodiment, when the first piercing element has been moved into the extended position, the first resilient element preferably holds the first piercing element in the extended position.

In one embodiment, the second piercing element may include a second resilient flange adapted to sequentially engage the second proximal projection and the second distal projection of the vial assembly housing when moving the second piercing element within the second guide channel from the retracted position to the extended position. When a force is applied to the proximal end of the second piercing element to slide the second piercing element toward the distal end of the vial housing, the second resilient element may flex for enabling the second piercing element to slide from the retracted position to the extended position. In one embodiment, when the second piercing element has been moved into the extended position, the second resilient element preferably holds the second piercing element in the extended position.

In one embodiment, the first piercing element may have a central opening at a proximal end thereof, and the first syringe may have a first dispensing tip projecting from the distal end thereof that is inserted into the central opening at the proximal end of the first piercing element.

In one embodiment, the second piercing element may have a central opening at a proximal end thereof, and the second syringe may have a second dispensing tip projecting from the distal end thereof that is inserted into the central opening at the proximal end of the second piercing element.

In one embodiment, the syringe assembly may include a dual barrel plunger including a first plunger rod inserted into a proximal end of the first syringe and a second plunger rod inserted into a proximal end of the second syringe. A tab (e.g., a thumb tab) may interconnect proximal ends of the first and second plunger rods.

In one embodiment, the dual barrel plunger is moveable toward a distal end of the syringe assembly for forcing the first liquid into the first vial and forcing the second liquid into the second vial.

In one embodiment, a vial assembly for a sealant delivery system may include a vial assembly housing having a proximal end and a distal end, the vial assembly housing having side-by-side first and second guide channels that extend between the proximal and distal ends of the vial assembly housing.

In one embodiment, a first vial is secured to the vial assembly housing. In one embodiment, the first vial has a proximal end that is aligned with the first guide channel and a first vial opening at the proximal end thereof that is closed by a first sealing membrane.

In one embodiment, the vial assembly includes a first piercing element disposed within the first guide channel and being moveable between a retracted position in which the first piercing element is located on a proximal side of the first sealing membrane and an extended position in which the first piercing element passes through the first sealing element for piercing the first sealing membrane.

In one embodiment, a second vial is secured to the vial assembly housing. In one embodiment, the second vial has a proximal end that is aligned with the second guide channel and a second vial opening at the proximal end thereof that is closed by a second sealing membrane.

In one embodiment, the vial assembly includes a second piercing element disposed within the second guide channel and being moveable between a retracted position in which the second piercing element is located on a proximal side of the second sealing membrane and an extended position in which the second piercing element passes through the second sealing element for piercing the second sealing membrane.

In one embodiment, the first piercing element has a proximal end and a distal end. In one embodiment, the first piercing element includes a central opening at the proximal end thereof that defines a first fluid pathway that extends along the length of the first piercing element.

In one embodiment, the first piercing element includes a first piercing spike that projects from the distal end of the first piercing element.

In one embodiment, the second piercing element has a proximal end and a distal end. In one embodiment, the second piercing element has a central opening that is located at the proximal end thereof that defines a second fluid pathway that extends along the length of the second piercing element.

In one embodiment, the second piercing element includes a second piercing spike that projects from the distal end of the second piercing element.

In one embodiment, the first and second fluid pathways that extend through the respective first and second piercing elements are isolated from one another.

In one embodiment, the vial assembly housing preferably includes a first proximal projection extending into the first guide channel that is adapted to contact the first piercing element for holding the first piercing element in the retracted position, and a first distal projection extending into the first guide channel that is adapted to contact the first piercing element for holding the first piercing element in the extended position.

In one embodiment, the vial assembly housing preferably includes a second proximal projection extending into the second guide channel that is adapted to contact the second piercing element for holding the second piercing element in the retracted position, and a second distal projection extending into the second guide channel that is adapted to contact the second piercing element for holding the second piercing element in the extended position.

In one embodiment, the first piercing element may include a first resilient flange adapted to sequentially engage the first proximal projection and the first distal projection of the vial assembly housing when moving the first piercing element within the first guide channel from the retracted position to the extended position.

In one embodiment, the second piercing element may include a second resilient flange adapted to sequentially engage the second proximal projection and the second distal projection of the vial assembly housing when moving the second piercing element within the second guide channel from the retracted position to the extended position.

In one embodiment, a sealant delivery system may include a vial assembly. In one embodiment, the sealant delivery system may have a syringe assembly including side-by-side first and second syringes, the first syringe having a first fluid chamber and the second syringe having a second fluid chamber.

In one embodiment, a distal end of the syringe assembly may be coupled with the proximal end of the vial assembly housing so that a distal end of the first syringe is aligned with the central opening at the proximal end of the first piercing element and a distal end of the second syringe is aligned with the central opening at the proximal end of the second piercing element.

In one embodiment, the first syringe has a first dispensing tip projecting from a distal end thereof that is in fluid communication with the first fluid compartment of the first syringe. In one embodiment, the first dispensing tip is inserted into the central opening at the proximal end of the first piercing element for providing fluid communication between the first fluid chamber and the first fluid pathway extending along the length of the first piercing element.

In one embodiment, the second syringe has a second dispensing tip projecting from a distal end thereof that is in fluid communication with the second fluid compartment of the second syringe. In one embodiment, the second dispensing tip is inserted into the central opening at the proximal end of the second piercing element for providing fluid communication between the second fluid chamber and the second fluid pathway extending along the length of the second piercing element.

In one embodiment, a first liquid is disposed in the first fluid chamber of the first syringe and a first powdered reactive component is disposed in the first vial of the vial assembly.

In one embodiment, when the first piercing element is moved into the extended position the first fluid pathway provides fluid communication between the first fluid chamber and the first vial.

In one embodiment, a second liquid is disposed in the second fluid chamber of the second syringe and a second powdered reactive component is disposed in the second vial of the vial assembly.

In one embodiment, when the second piercing element is moved into the extended position the second fluid pathway provides fluid communication between the second fluid chamber and the second vial;

In one embodiment, a sealant delivery system preferably includes a syringe assembly including side-by-side first and second syringes, the first syringe having a first fluid chamber containing a first liquid and the second syringe having a second fluid chamber containing a second fluid.

In one embodiment, the sealant delivery system may include a vial assembly coupled to a distal end of the syringe assembly, the vial assembly including side-by-side first and second vials.

In one embodiment, the first vial contains a first powdered reactive component. In one embodiment, the first vial has a proximal end that is aligned with a distal end of the first syringe and a first vial opening at the proximal end thereof that is closed by a first sealing membrane.

In one embodiment, the second vial contains a second powdered reactive component. In one embodiment, the second vial has a proximal end that is aligned with a distal end of the second syringe and a second vial opening at the proximal end thereof that is closed by a second sealing membrane.

In one embodiment, the vial assembly preferably includes a first piercing element located between the distal end of the first syringe and the first sealing membrane. In one embodiment, the first piercing element is moveable between a retracted position in which the first piercing element is located on a proximal side of the first sealing membrane and an extended position in which the first piercing element pierces the first sealing membrane to provide fluid communication between the first fluid chamber and the first vial.

In one embodiment, the vial assembly preferably includes a second piercing element located between the distal end of the second syringe and the second sealing membrane. In one embodiment, the second piercing element is moveable between a retracted position in which the second piercing element is located on a proximal side of the second sealing membrane and an extended position in which the second piercing element pierces the second sealing membrane to provide fluid communication between the second fluid chamber and the second vial.

In one embodiment, the syringe assembly may include a dual barrel plunger including a first plunger rod inserted into a proximal end of the first syringe and a second plunger rod inserted into a proximal end of the second syringe.

In one embodiment, a tab interconnects proximal ends of the first and second plunger rods.

In one embodiment, the dual barrel plunger is moveable toward a distal end of the syringe assembly for forcing the first liquid into the first vial for reconstituting the first powdered reactive component to generate a first solution and forcing the second liquid into the second vial for reconstituting the second powdered reactive component to generate a second solution.

The first and second solutions may be mixed together for forming a sealant or hemostat that may be applied on tissue.

In one embodiment, the dual barrel plunger may be repeatedly reciprocated in distal and proximal directions (e.g., back and forth) to expedite the solution mixing process (e.g., reconstituting the powdered reactive components). In one embodiment, the dual barrel plunger may be repeatedly reciprocated in proximal and distal directions about 20, 30, 40, or more cycles. The dual barrel plunger is preferably reciprocated back and forth until the first liquid has been completely mixed with the first powdered reactive component and the second liquid has been completely mixed with the second powdered reactive component.

In one embodiment, after the first and second reactive powdered components have been reconstituted, the dual barrel plunder may be retracted for drawing the first solution into the first syringe and the second solution into the second syringe. At this stage, the first and second solutions preferably remain isolated from one another.

In one embodiment, the vial assembly housing may include side-by-side first and second guide channels (e.g., cavities) that extend between proximal and distal ends of the vial assembly housing.

In one embodiment, the vial assembly housing includes a first proximal projection extending into the first guide channel that is adapted to contact the first piercing element for holding the first piercing element in the retracted position, and a first distal projection extending into the first guide channel that is adapted to contact the first piercing element for holding the first piercing element in the extended position.

In one embodiment, the vial assembly housing includes a second proximal projection extending into the second guide channel that is adapted to contact the second piercing element for holding the second piercing element in the retracted position, and a second distal projection extending into the second guide channel that is adapted to contact the second piercing element for holding the second piercing element in the extended position.

In one embodiment, a powder vial may contain about 0.1-2 grams of powder. In one embodiment, a powder vial may contain about 0.4-0.5 drams and more preferably about 0.408 grams of a powdered reactive component.

In one embodiment, a vial may have a size of about 2-10 ml, more preferably about 3-5 ml, and even more preferably about 4 ml.

In one embodiment, a vial may be made of glass or polymer materials (e.g., plastic).

There and other preferred embodiments of the present patent application will be described in more detail below.

BRIEF DESCRIPTION OF THE DRAWINGS

FIG. 4A is a top, cross-sectional view of the syringe assembly shown in FIG. 2.

FIG. 4B is a side, cross-sectional view of the syringe assembly shown in FIG. 2

FIG. 6 is an exploded view of the vial assembly shown in FIGS. 5A and 5B.

DETAILED DESCRIPTION OF PREFERRED EMBODIMENTS

Figure 1:
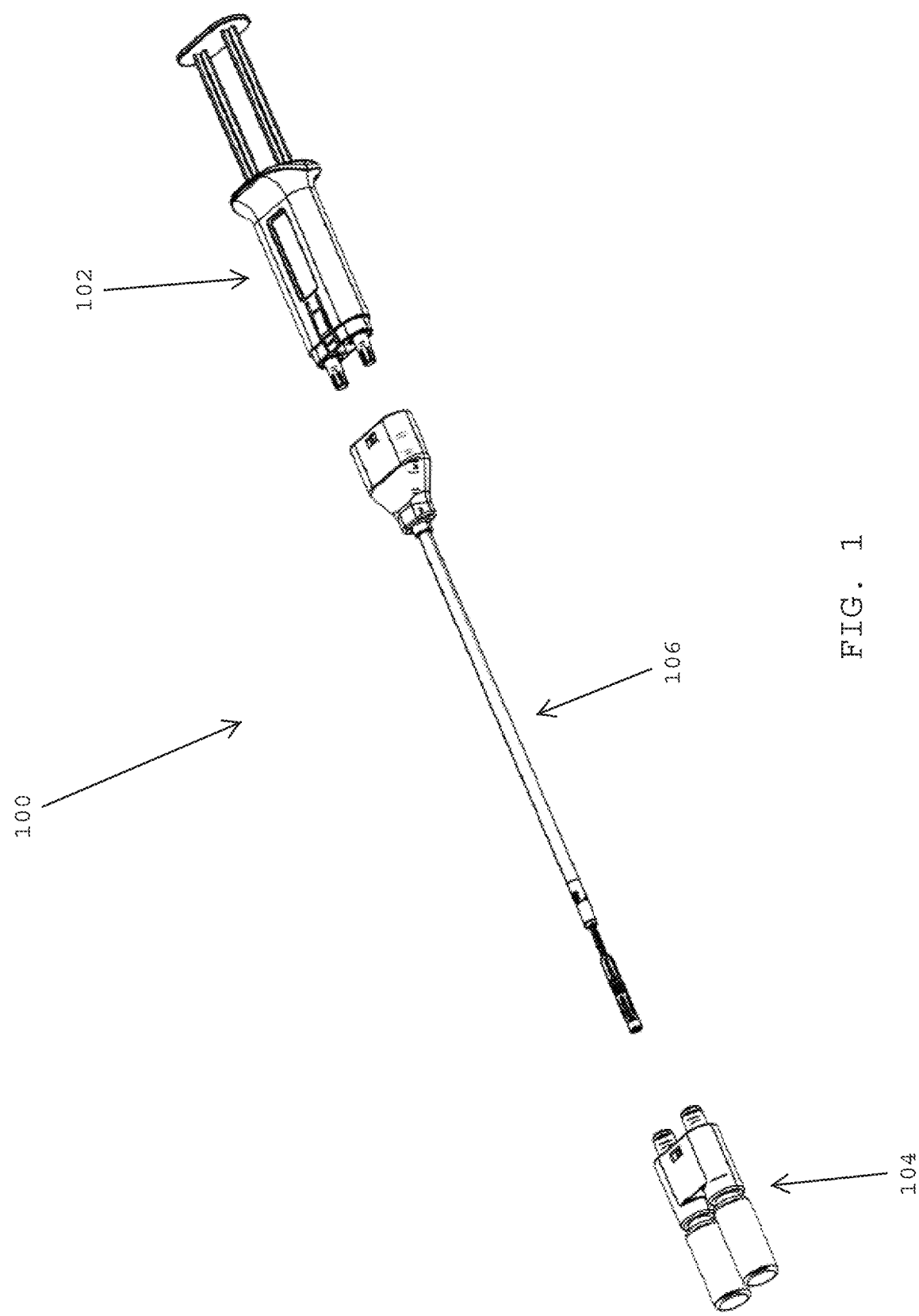
FIG. 1 is a perspective view of the components of a sealant delivery system including a syringe assembly, a sealant delivery assembly, and a vial assembly, in accordance with one embodiment of the present patent application.

Referring to FIG. 1, in one embodiment, a sealant delivery system 100 for dispensing a tissue sealant (e.g., a hemostat; a sealant for sealing air leaks during lung surgery) preferably includes a syringe assembly 102, a vial assembly 104, and a sealant delivery assembly 106. In one embodiment, the syringe assembly 102 may include first and second syringes, whereby each syringe contains a liquid (e.g., a diluent; a buffer solution; a catalyst; an initiator; an activation fluid, etc.). In one embodiment, the vial assembly 104 may include first and second vials, whereby each vial contains a reactive powder component (e.g.; a fibrinogen powder; a thrombin powder; a reactive synthetic powder; a crosslinker, etc.), as will be described in more detail herein.

Figure 2:
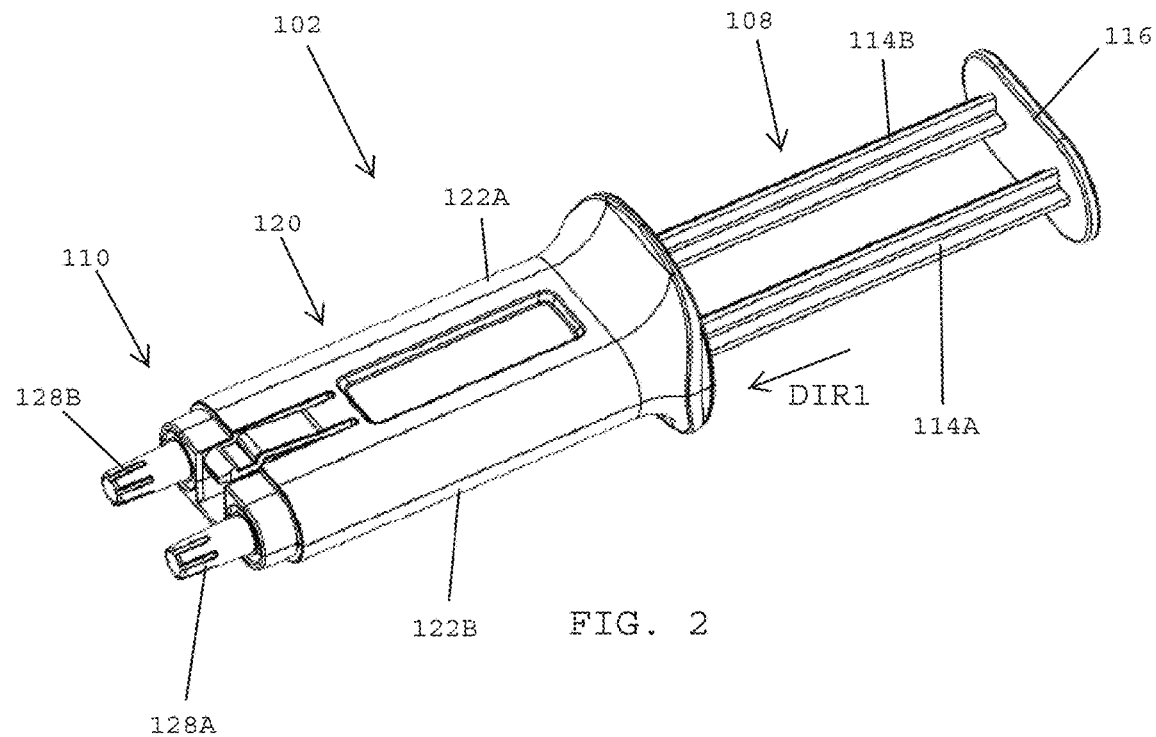
FIG. 2 is a perspective view of the syringe assembly shown in FIG. 1.
Figure 3:
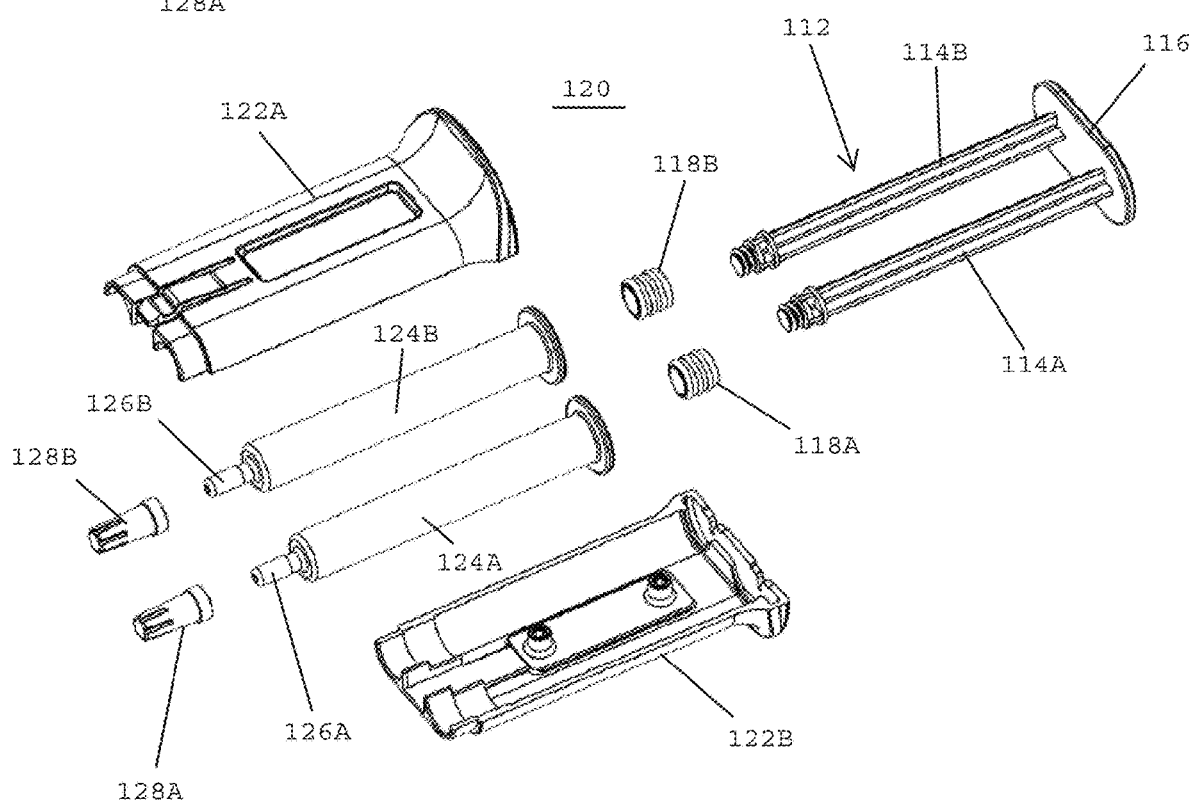
FIG. 3 is an exploded view of the syringe assembly shown in FIG. 2.

Referring to FIGS. 2 and 3, in one embodiment, the syringe assembly 102 preferably has a proximal end 108 and a distal end 110. In one embodiment, the syringe assembly 102 includes a dual barrel plunger 112 having a first plunger rod 114A and a second plunger rod 114B. In one embodiment, the proximal ends of the first and second plunger rods 114A, 114B are connected to a depressible thumb tab 116, which may be utilized by surgical personnel (e.g., a surgeon) for depressing the plunger rods 114A, 114B in the direction DIR1 toward the distal end 110 of the syringe assembly 102 (e.g., to express one or more sealant precursors from the distal of the syringe assembly).

In one embodiment, the syringe assembly 102 preferably includes a first plunger 118A secured to a distal end of the first plunger rod 114A, and a second plunger 1188 secured to a distal end of the second plunger rod 114B, The first and second plungers 118A, 118B preferably have outer perimeters that form fluid-tight seals with inner surfaces of first and second syringe barrels, as will be described in more detail herein.

In one embodiment; the syringe assembly 102 preferably includes a syringe assembly housing 120 including a first housing part 122A and a second housing part 122B that are configured for being connected together. In one embodiment, the first and second housing parts 122A, 122B may be snap-fit together.

In one embodiment, the syringe assembly housing 120 is preferably adapted to hold a first syringe 124A and a second syringe 124B. The first and second syringes 124A, 124B are preferably configured for containing fluids (e.g., a diluent; a buffer solution; a catalyst; an initiator; an activation fluid, etc.) that are mixed with the reactive powder components disposed within the respective first and second vials of the vial assembly 104 (FIG. 1).

In one embodiment, the first syringe 124A is configured to receive a distal end of the first plunger rod 114A and the first plunger 118A that is secured to the distal end of the first plunger rod. In one embodiment, the second syringe 124B is configured to receive a distal end of the second plunger rod 114B and the second plunger 118B that is secured to the distal end of the second plunger rod.

Referring to FIG. 3, in one embodiment, the distal end of the first syringe 124A has a first dispensing tip 126A with an opening for dispensing a first fluid contained within a first fluid chamber (not shown) of the first syringe, and the distal end of the second syringe 124B has a second dispensing tip 126B with an opening for dispensing a second fluid contained within a second fluid chamber (not shown) of the second syringe.

In one embodiment, the syringe assembly 102 preferably includes first and second end caps 128A, 128B that are adapted to be releasably secured over the first and second dispensing tips 126A, 126B located at distal ends of the respective first and second syringes 124A, 124B.

In one embodiment, after the first and second end caps 128A, 128B are removed from the respective first and second dispensing tips 126A, 128B of the first and second syringes 124A, 124B, the thumb tab 116 may be depressed in the direction DIR1 (FIG. 2) toward the distal end of the syringe assembly, whereupon the first and second fluids (e.g., a diluent; a buffer solution; a catalyst; an initiator; an activation fluid, etc.) contained within the fluid chambers of the respective first and second syringes 124A, 124B are dispensed from the first and second dispensing tips 126A, 126B.

Referring to FIGS. 4A and 4B, in one embodiment, the syringe assembly 102 preferably includes the first syringe 124A and the second syringe 124B that are positioned side-by-side between the first housing part 122A and the second housing part 122B of the syringe assembly housing 120. The first syringe 124A preferably has a first fluid chamber 130A that is configured to receive a first liquid (e.g., a diluent; a buffer solution; a catalyst; an initiator; an activation fluid, etc.). The second syringe 124B preferably includes a second fluid chamber 130B that is configured to receive a second liquid (e.g., a diluent; a buffer solution; a catalyst; an initiator; an activation fluid, etc.). In one embodiment, the first and second fluids contained within the respective first and second fluid chambers 130A, 130B may have the same properties or different properties.

In one embodiment, the distal end of the dual barrel plunger 112 is preferably assembled with the proximal ends of the respective first and second syringes 124A, 124B so that the first plunger 118A and the distal end of the first plunger rod 114A are inserted into the proximal end of the first syringe 124A and the second plunger 118B and the distal end of the second plunger rod 114B are inserted into the proximal end of the second syringe 124B.

In one embodiment, the first end cap 128A is preferably secured over the first dispensing tip 126A of the first syringe 124A, and the second end cap 128B is preferably secured over the second dispensing tip 126B of the second syringe 124B. The end caps may remain over the dispensing tips during storage and prior to use, and may be removed from covering the end caps immediately prior to use during a surgical procedure.

In one embodiment, the first and second end caps 128A, 128B may be removed from the distal end 110 of the syringe assembly 102 for exposing the dispensing tips 126A, 126B located at the distal ends of the respective first and second syringes 124A, 124B. In one embodiment, the thumb tab 116 of the dual barrel plunger 112 may be depressed in the distal direction DIR1 toward the distal end 110 of the syringe assembly 102 for dispensing and/or expressing the first and second liquids (e.g., a diluent; a buffer solution; a catalyst; an initiator; an activation fluid, etc.) contained within the first and second fluid chambers 130A, 130B of the respective first and second syringes 124A, 124B. In one embodiment, the first and second liquids are utilized for reconstituting and mixing the powder components that are contained within the first and second vials of the vial assembly 104 (FIG. 1).

As will be described in more detail herein, in one embodiment, after the activation fluids have been initially forced into the vials of the vial assembly, the thumb tab 116 and the dual barrel plunger 112 may be retracted in the proximal direction designated DIR2 for drawing solutions and/or mixtures of the activation fluids and the powdered reactive components back into the fluid chambers 130A, 130B of the respective first and second syringes 124A, 124B for further mixing together of the activation fluids and the powdered reactive components.

Certain types of therapeutic components must be stored in a powdered form because they will rapidly react and/or lose their effectiveness once they are mixed into a liquid or a solution. These therapeutic components are required to be reconstituted with a liquid (e.g., a diluent; a buffer solution; a catalyst; an initiator; an activation fluid, etc.) before they may be used on a patient. The first and second liquids in the syringes may be used to activate the reactive powdered components contained within the vial assembly to form a tissue sealant or a hemostat that may be sprayed and/or expressed onto tissue. In one embodiment, the first liquid is used to reconstitute a first reactive powder component (e.g., fibrinogen in powder form; a reactive synthetic powder; a crosslinker, etc.), and the second liquid is used to reconstitute a second reactive powder component (e.g., thrombin in powder form; a reactive synthetic powder; a crosslinker, etc.).

Figure 5A:
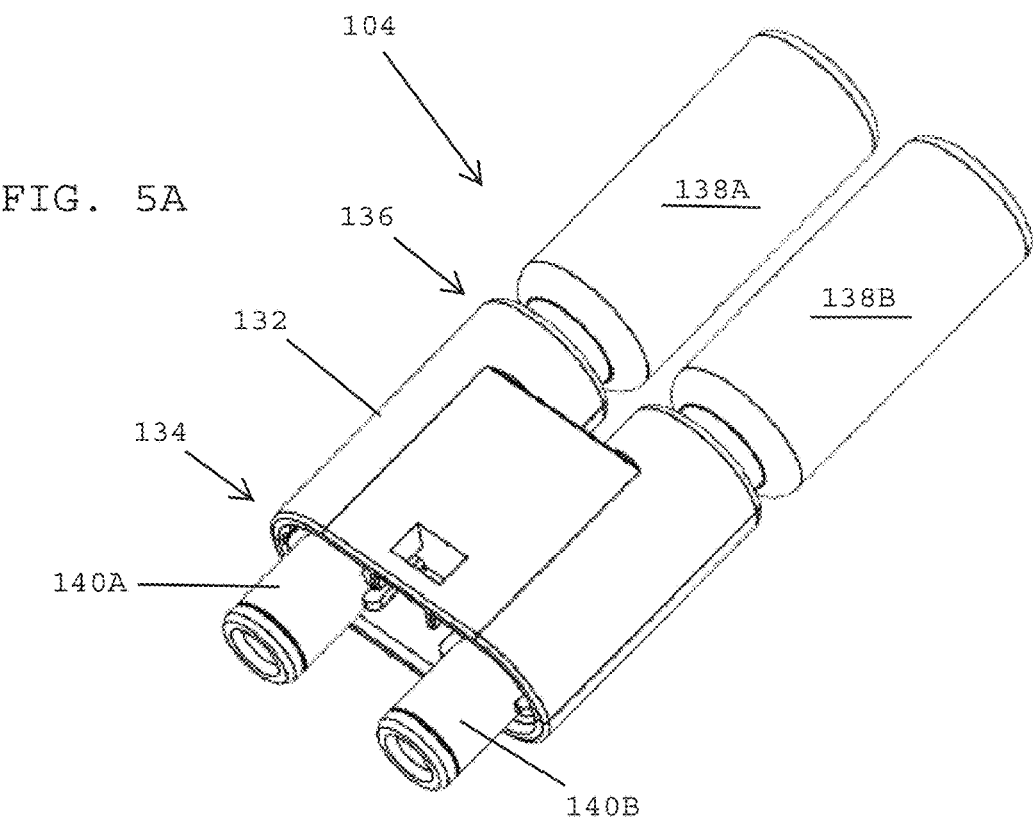
FIG. 5A is a perspective view of the vial assembly shown in FIG. 2.
Figure 5B:
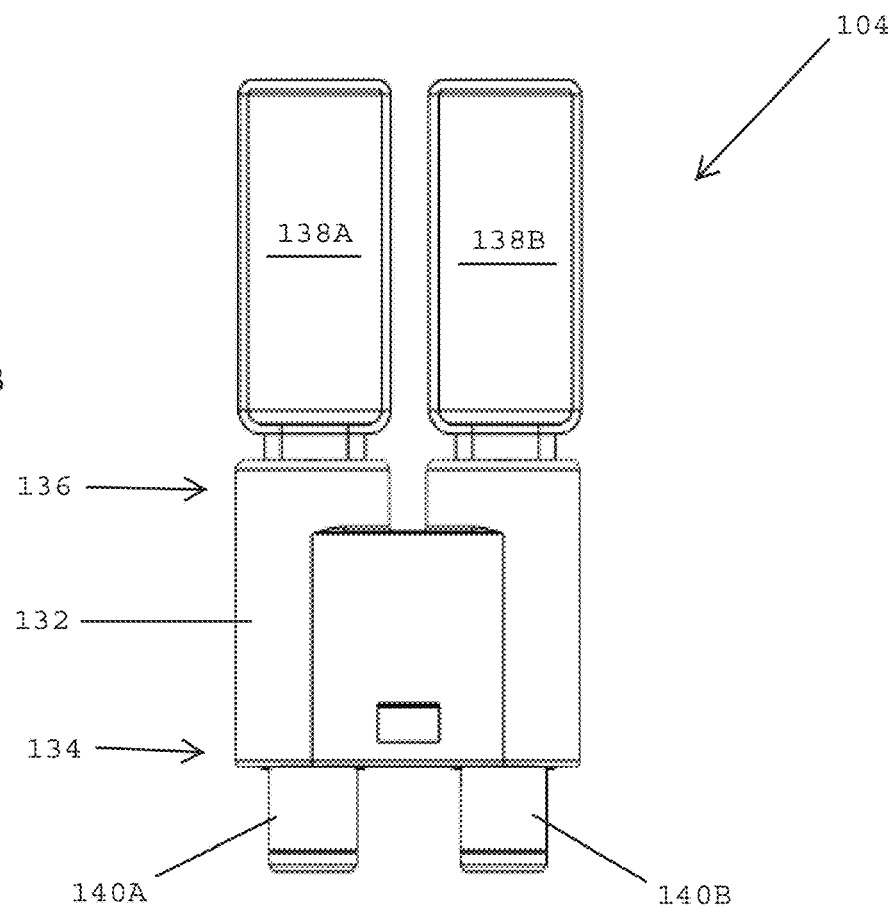
FIG. 5B is a front elevation view of the vial assembly shown in FIG. 5A.

Referring to FIGS. 5A and 5B, in one embodiment, a vial assembly 104 (FIG. 1) of a sealant delivery system preferably includes a vial assembly housing 132 having a proximal end 134 and a distal end 136. In one embodiment, the vial assembly 104 desirably includes first and second vials 138A, 138B that are configured to contain powdered reactive components that are mixed together using liquids (e.g., a diluent; a buffer solution; a catalyst; an initiator; an activation fluid, etc.) contained within the first and second syringes of the syringe assembly. In one embodiment, the first and second vials 138A, 138B are preferably secured to the distal end 136 of the vial assembly housing 132. In one embodiment, the first vial 138A may contain a first reactive powder component (e.g., fibrinogen powder; a reactive synthetic powder; a crosslinker, etc.), and the second vial 138B may contain a second reactive powder component (e.g., thrombin powder; a reactive synthetic powder; a crosslinker, etc.). In one embodiment, the vial assembly 104 preferably includes a first piercing element 140A having a first piercing spike (not shown) that is aligned with a first vial opening at a proximal end of the first vial 138A, and a second piercing element 140B having a second piercing spike (not shown) that is aligned with a second vial opening at a proximal end of the second vial 138B.

In one embodiment, the first and second piercing elements 140A, 140B are moveable between retracted and extended positions. In one embodiment, the first and second piercing elements move independently of one another. In one embodiment, the first and second piercing elements move simultaneously with one another.

The vial assembly 104 is designed to maintain the first and second reactive powdered components isolated from one another during storage of the vial assembly and prior to use of the powdered components for forming a therapeutic solution (e.g., a tissue sealant; a hemostat; a sealant for sealing air leaks during lung surgery).

Referring to FIG. 6, in one embodiment, the vial assembly 104 desirably includes the vial assembly housing 132 having a first housing part 142A, and a second housing part 142B. In one embodiment, the first and second housing parts 142A, 142B are adapted for being snap-fit together to form the vial assembly housing. In one embodiment, when the first and second housing parts 142A, 142B are assembled together, the vial assembly housing 132 is adapted to contain the first and second piercing elements 140A, 140B, whereby the first and second piercing elements may slide relative to the vial assembly housing between retracted and extended positions, as will be described in more detail herein.

In one embodiment, the vial assembly 104 preferably includes a first powder vial 138A having a proximal end 144A with a first vial opening 146A, and a first sealing membrane 148A that covers and/or seals the first vial opening 146A. During storage and prior to use, the first sealing membrane 148A preferably maintains a first powder (e.g., a first powdered reactive component) that is disposed within the first powder vial 138A in a dry state. The vial assembly 104 preferably includes a first sealing ring 150A having a central opening 152A that is configured to receive a first piercing spike 154A that projects from a distal end of the first piercing element 140A. In one embodiment, the vial assembly 104 includes a first O-ring 156A that is inserted into an opening at a proximal end of the first piercing element 140A, and a first O-ring retainer 158A that preferably retains the first O-ring 156A within the openings at the proximal end of the first piercing element 140A.

In one embodiment, the vial assembly 104 preferably includes a second powder vial 188B having a proximal end 144B with a second vial opening 146B, and a second sealing membrane 148B that covers and/or seals the second vial opening 146B. During storage and prior to use, the second sealing membrane 148B preferably maintains a second powder (e.g., a second powdered reactive component) that is disposed within the second powder vial 138B in a dry state. The vial assembly 104 preferably includes a second sealing ring 150B having a central opening 152B that is configured to receive a second septum piercing spike 154B that projects from a distal end of the second piercing element 140B. In one embodiment, the vial assembly 104 includes a second O-ring 156B that is inserted into an opening at a proximal end of the second piercing element 140B, and a second O-ring retainer 158B that preferably retains the second O-ring 156B within the opening at the proximal end of the second piercing element 140B.

In one embodiment, the first and second housing parts 142A, 142B of the vial housing 132 are molded components that have guide channels 145A, 145B that extend side-by-side between the proximal and distal ends of the vial housing 132. The guide channels 145A, 145B are preferably configured to receive the respective first and second piercing elements 140A, 140B for guiding the sliding movement of the first and second piercing elements between the retracted and extended positions. When the first and second piercing elements 140A, 140B are disposed within the vial housing 132, the first and second piercing elements 140A, 140B may slide and/or move between a retracted position and an extended position. In one embodiment, when the first and second piercing elements are in the extended position, the first and second piercing spikes 154A, 154B pierce the respective first and second sealing membranes 140A, 140B that seal the first and second vial openings 146A, 146B of the respective first and second vials 138A, 138B.

Figure 7:
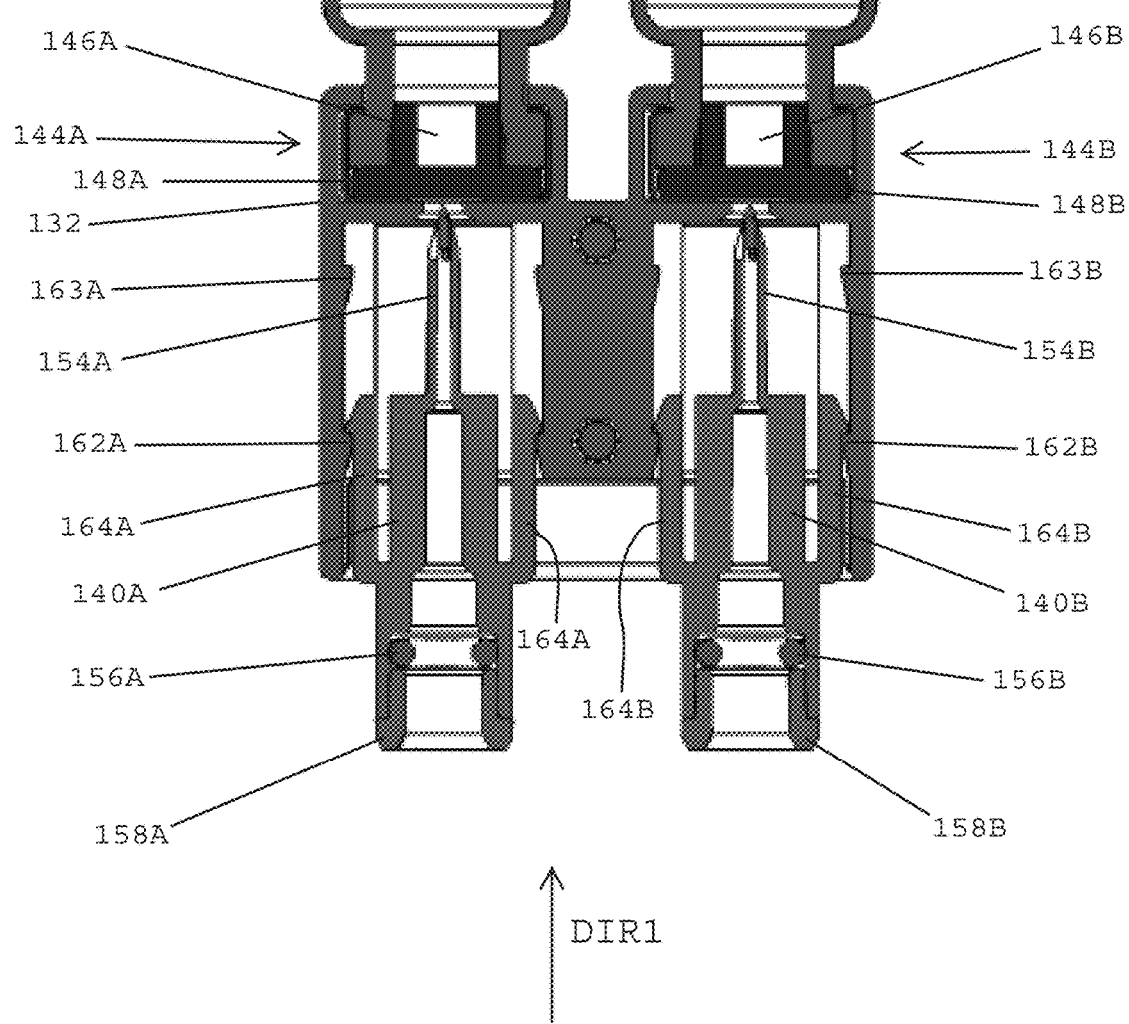
FIG. 7 is a cross-sectional view of the vial assembly shown in FIGS. 5A and 5B.

Referring to FIG. 7, in one embodiment, the vial assembly 104 preferably includes the first vial 138A secured to the distal end 136 of the vial assembly housing 132. The first sealing membrane 148A covers and/or seals the first vial opening 146A located at the proximal end 144A of the first vial 138A. The first piercing element 140A is assembled with the vial assembly housing 132 so that the first piercing spike 154A of the first piercing element 140A is aligned with the first sealing membrane 148A that covers and/or seals the first vial opening 146A of the first vial 138A.

In one embodiment, the vial assembly 104 preferably includes the second vial 138B secured to the distal end 136 of the vial assembly housing 132. The second sealing membrane 148B covers and/or seals the second vial opening 140B located at the proximal end 144B of the second vial 138B. The second piercing element 140B is assembled with the vial assembly housing 132 so that the second piercing spike 154B of the second piercing element 140B is aligned with the second sealing membrane 148B that covers and/or seals the second vial opening 146B of the second vial 138B.

Figure 8:
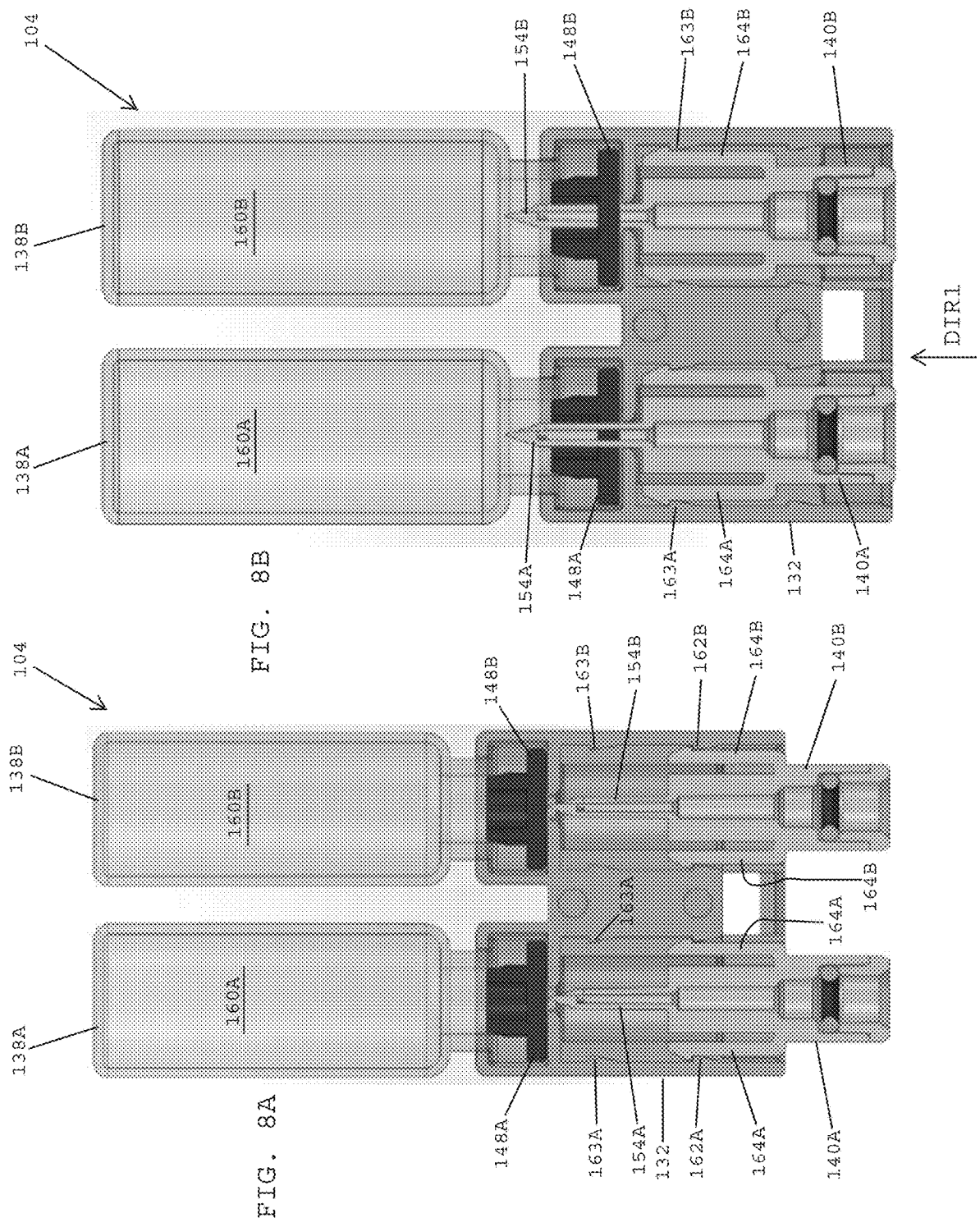
FIG. 8A shows the vial assembly of FIG. 7 with first and second piercing elements in retracted positions, in accordance with one embodiment of the present patent application.
FIG. 8B shows the vial assembly of FIG. 8A with the first and second piercing elements in extended positions for piercing first and second sealing membranes that seal vial openings of respective first and second vials, in accordance with one embodiment of the present patent application.

In one embodiment, the vial assembly housing 132 preferably includes first proximal projections 162A for locking and/or holding the first piercing element 140A is the retracted position and first distal projections 163A for locking and/or holding the first piercing element in the extended position. In one embodiment, the first piercing element 140A preferably includes first resilient flanges 164A that are adapted to selectively engage the first proximal projections 162A and the first distal projections 163A. In one embodiment, when the first piercing element 140A is in the retracted position shown in FIG. 7, the first resilient flanges 164A desirably engage the first proximal projections 162A for holding the first piercing element 140A in the retracted position. In one embodiment, the first piercing element 140A may be slid and/or pressed in the distal direction DIR1, whereupon the first resilient flanges 164A release from the first proximal projections 162A and slide into engagement with the first distal projections 163A for locking and/or holding the first piercing element 140A in the extended position (FIG. 8B).

In one embodiment, the vial assembly housing 132 preferably includes second proximal projections 162B for locking and/or holding the second piercing element 140B in the retracted position and second distal projections 163B for locking and/or holding the second piercing element 140B in the extended position. In one embodiment, the second piercing element 140B preferably includes second resilient flanges 164B that are adapted to selectively engage the second proximal projections 162B and the second distal projections 163B. In one embodiment, when the second piercing element 140B is in the retracted position shown in FIG. 7, the second resilient flanges 164B engage the second proximal projections 162B for holding the second piercing element 140B in the retracted position. In one embodiment, the second piercing element 140B may be slid and/or pressed in the distal direction DIR1, whereupon the second resilient flanges 164B release from the second proximal projections 162B and slide into engagement with the second distal projections 163B for locking and/or holding the second piercing element 146B in the extended position (FIG. 8B).

In one embodiment, when the first piercing element 140A is assembled with the vial assembly housing 132, the first piercing spike 154A is in alignment with the first sealing membrane 148A that seals the first vial opening 146A of the first vial 138A. When the first piercing element 140A is advanced into the extended position (FIG. 8B), the first piercing spike 154A pierces the first sealing membrane 148A for providing fluid communication between the first liquid contained within the first fluid chamber of the first syringe 124A (FIG. 4A) and the first powder (e.g., a first powdered reactive component) contained within the first powder chamber 160A of the first vial 138A.

In one embodiment, when the second piercing element 140B is assembled with the vial assembly housing 132, the second piercing spike 154E is in alignment with the second sealing membrane 148B that seals the second vial opening 146B of the second vial 138B. When the second piercing element 140B is advanced into the extended position (FIG. 8B), the second piercing spike 154B pierces the second sealing membrane 148B for providing fluid communication between the second liquid contained within the second fluid chamber of the second syringe 124B (FIG. 4A) and the second powder (e.g., a second powdered reactive component) contained within the second powder chamber 160B of the second vial 138B.

In one embodiment, the first piercing element 140A has an elongated conduit that defines a first fluid pathway that extends through both the first piercing element and the first piercing spike 154A for providing fluid communication between the first fluid chamber of the first syringe and the powder chamber 160A of the first vial 138A, which enables the first liquid to be used for reconstituting the first powder disposed within the first vial. In one embodiment, a first O-ring 156A is inserted into an opening at a proximal end of the first piercing element 140A and a first O-ring retainer 158A holds the first O-ring 156A within the proximal opening of the first piercing element 140A.

In one embodiment, the second piercing element 140B has an elongated conduit that defines a second fluid pathway that extends through both the second piercing element and the second piercing spike 154B for providing fluid communication between the second fluid chamber of the second syringe and the second powder chamber 160B of the second vial 138B, which enables the second liquid to be used for reconstituting the second powder (e.g., a second powdered reactive component) disposed within the second vial. In one embodiment, a second O-ring 156B is inserted into an opening at a proximal end of the second piercing element 140B and a second O-ring retainer 158B holds the second O-ring 156B within the proximal opening of the second piercing element 140B.

Referring to FIG. 8A, in one embodiment, the vial assembly 104 preferably includes the first and second vials 138A, 138B secured to the distal end 136 of the vial assembly housing 132. In one embodiment, the first vial 138A includes a first powder chamber 160A that is configured to contain a first powder (e.g., a first powdered reactive component; a fibrinogen powder; a thrombin powder; a crosslinker, etc.), and the second vial 138B includes a second powder chamber 160B that is configured to contain a second powder (e.g., a second reactive powder; a fibrinogen powder; a thrombin powder; a crosslinker, etc.). In FIG. 8A, the first piercing element 140A is in the retracted position with the first piercing spike 154A located proximal to the first sealing membrane 148A. The first piercing element 140A includes the first resilient flanges 164A engaging the first proximal projections 162A of the vial housing 132 for holding the first piercing element 140A in the retracted position. The vial assembly 104 includes the first distal projections 163A that are adapted to engage the distal ends of the first resilient flanges 164A for holding the first piercing element 140A in the extended configuration, as will be described in more detail herein.

In one embodiment, the second piercing element 140B is in the retracted position with the second piercing spike 154B located proximal to the second sealing membrane 148B. The second piercing element 140B includes the second resilient flanges 184B engaging the second proximal projections 162B of the vial housing 132 for holding the second piercing element 140B in the retracted position. The vial assembly 104 includes the second distal projections 163B that are adapted to engage the distal ends of the second resilient flanges 164B for holding the second piercing element 140B in the extended configuration, as will be described in more detail herein.

Referring to FIG. 8B, in one embodiment, the first and second piercing elements 140A, 140B may be advanced in the distal direction DIR1 toward the distal end 136 of the vial assembly housing 132 for moving the first and second piercing elements into the extended position. In the extended position shown in FIG. 8B, the first piercing spike 154A pierces the first sealing membrane 148A, and the second piercing spike 154B pierces the second sealing membrane 148B. The first resilient flanges 162A of the first piercing element 140A engage the first distal projections 163A of the vial assembly housing 132 for holding and/or locking the first piercing element 140A in the extended position, and the second resilient flanges 162B of the second piercing element 140B engage the second distal projections 163B of the vial assembly housing 132 for holding and/or locking the second piercing element 140B in the extended position.

Figure 9:
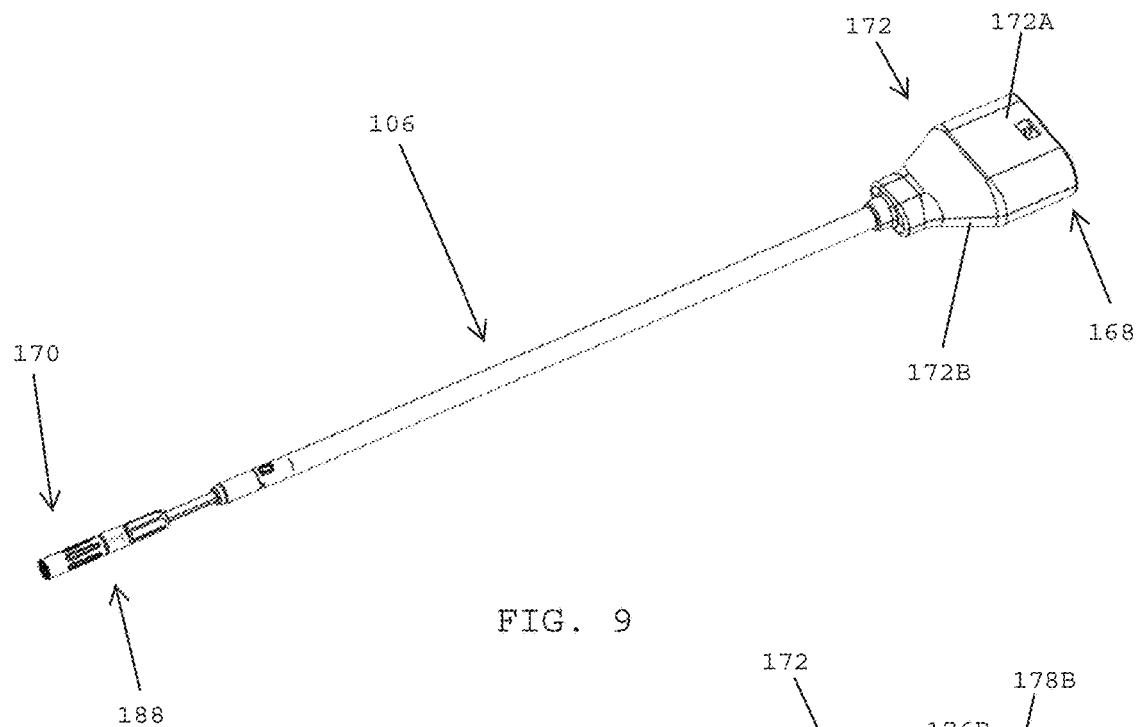
FIG. 9 is a perspective view of the sealant delivery assembly shown in FIG. 1.
Figure 10:
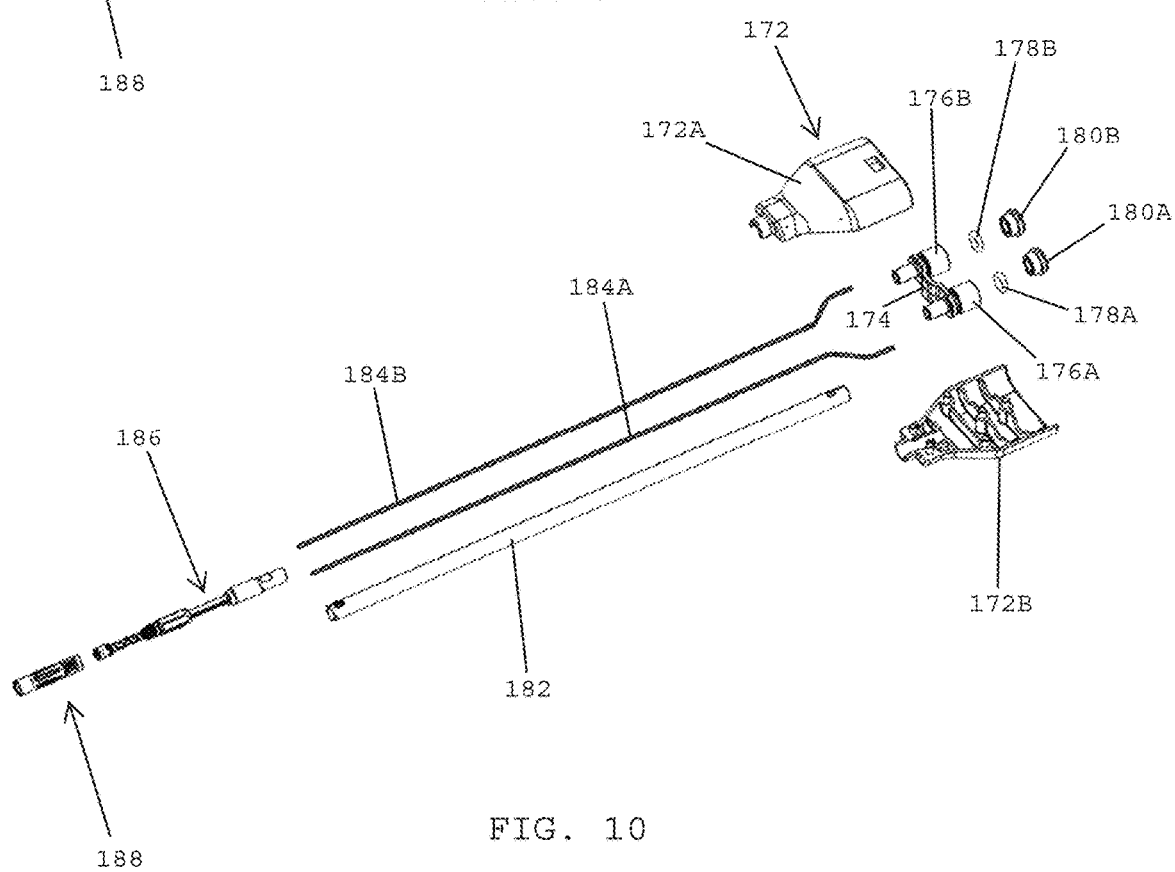
FIG. 10 is an exploded view of the sealant delivery assembly shown in FIG. 9.

Referring to FIGS. 9 and 10, in one embodiment, the sealant delivery assembly 106 of the sealant delivery system 100 (FIG. 1) preferably includes a proximal end 168 that is configured for being connected with a distal end of the syringe assembly 102 (FIG. 1) and a distal end 170 that is adapted to express and/or spray a tissue sealant (e.g., a hemostat; a sealant for sealing air leaks during lung surgery). In one embodiment, the proximal end 168 of the sealant delivery assembly 106 desirably includes a sealant delivery assembly housing 172 having a first housing part 172A and a second housing part 172B, which may be snap-fit together.

In one embodiment, the housing 172 preferably includes an H-connector 174 having a first hub 176A adapted to receive a first O-ring 178A and a first O-ring retainer 180A. In one embodiment, the first hub 176A, the first O-ring 178A, and the first O-ring retainer 180A are preferably in alignment with the first fluid pathway that provides fluid communication between the first fluid compartment 130A of the first syringe 124A (FIG. 4A) and the distal end of the sealant delivery assembly 106.

In one embodiment, the H-connector 174 preferably includes a second hub 176B adapted to receive a second O-ring 178B and a second O-ring retainer 180B. In one embodiment, the second hub 176B, the second O-ring 178B, and the second O-ring retainer 180B are preferably in alignment with the second fluid pathway that provides fluid communication between the second fluid compartment 130B of the second syringe 124B (FIG. 4A) and the distal end of the sealant delivery assembly 106.

In one embodiment, the sealant delivery assembly 106 preferably includes a cannula 182 (e.g., a rigid tube) that is adapted to receive first and second flexible tubes 184A, 184B. The cannula may be rigid and may be made of biocompatible materials such as metals and polymers. The first flexible tube 184A preferably has a proximal end that is in fluid communication with the first hub 176A of the H-connector 174. The second flexible tube 184B preferably has a proximal end that is in fluid communication with the second hub 176B of the H-connector 174.

In one embodiment, the sealant delivery assembly 106 desirably includes a malleable connector 186 that is secured to a distal end of the cannula 182. The sealant delivery assembly 106 preferably includes a spray tip 188 that is secured to a distal end of the malleable connector 186. The spray tip 188 may contain a static mixer for mixing together first and second precursor solutions that are directed into the spray tip 188.

Figure 11:
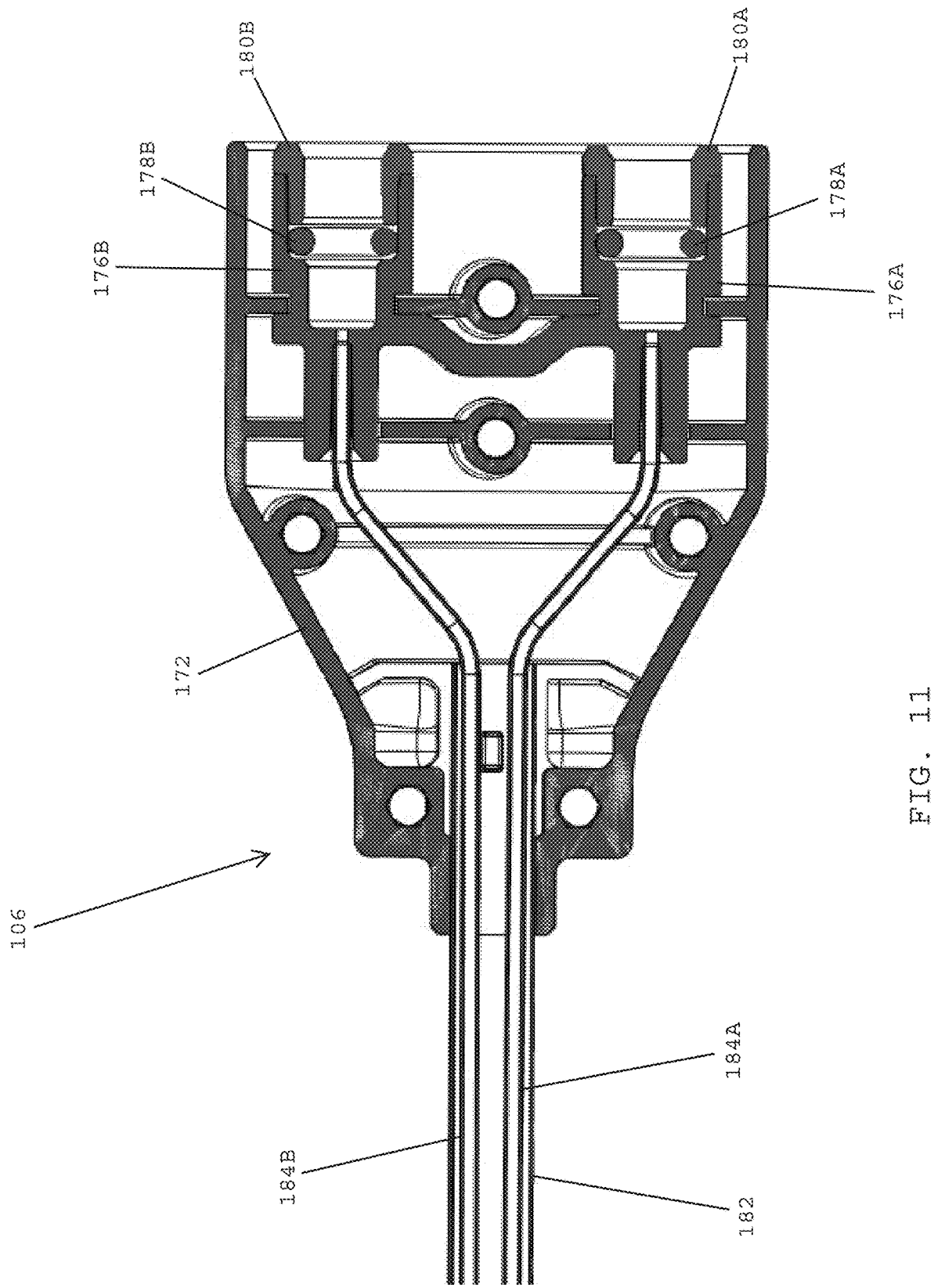
FIG. 11 is a top, cross-sectional view of a proximal end of the sealant delivery assembly shown in FIG. 9.

Referring to FIG. 11, in one embodiment, the proximal end of the elongated cannula 182 is assembled with a distal end of the sealant delivery assembly housing 172. The first and second flexible tubes 184A, 184B extend through an elongated conduit of the cannula 182. A proximal end of the first flexible tube 184A is in fluid communication with the first hub 176A. A proximal end of the second flexible tube 184B is in fluid communication with the second hub 176B. The first O-ring 178A is inserted into the first hub 176A and is held in place by the first O-ring retainer 180A. The second O-ring 178B is inserted into the second hub 176B and is held in place by the second O-ring retainer 180B.

Figure 12:
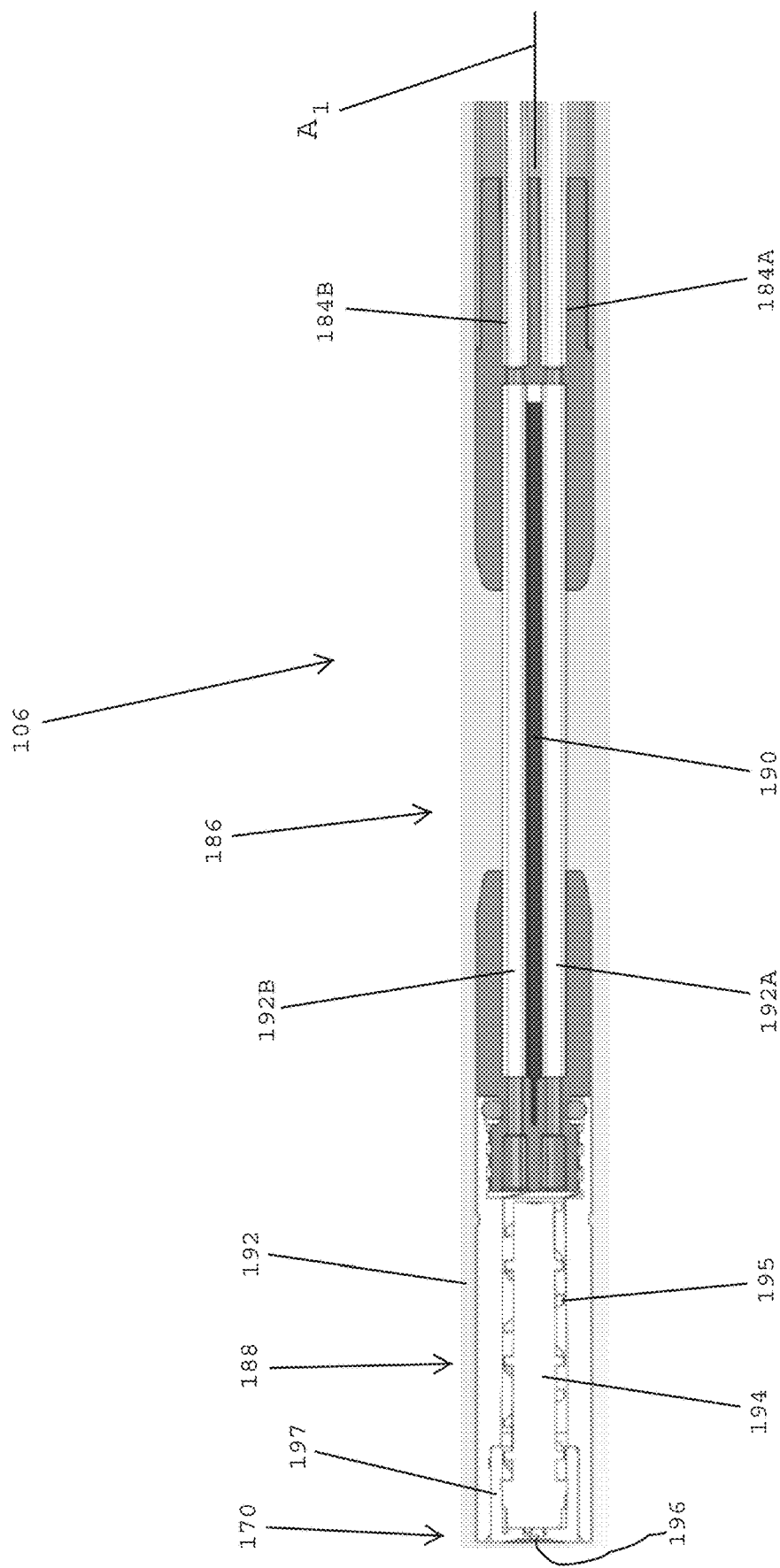
FIG. 12 is a cross-sectional view of a distal end of the sealant delivery system shown in FIG. 9 including a spray tip.

Referring to FIG. 12, in one embodiment, the malleable connector 186 at the distal end of the sealant delivery assembly 106 preferably couples the spray tip 188 with the distal end of the cannula 182. The malleable connector 186 desirably includes a malleable component 190 (e.g., a malleable metal rod; a malleable pin) disposed therein that enables the spray tip 188 to be positioned and held at different angles relative to the longitudinal axis $A_1$ of the cannula 182.

In one embodiment, the spray tip 188 preferably includes a spray tip housing 192 that contains a static mixer 194 having mixing fins 195. The first and second precursor solutions that are delivered to the spray tip 188 via the first and second flexible tubes 184A, 184B are preferably mixed together within the spray tip housing 194 by the mixing fins 195 of the static mixer 192. The mixed precursor solutions may be expressed and/or sprayed from the distal end of the sealant applicator via an expression opening 196 of a spray cap 197, which is located at the distal end 170 of the sealant delivery assembly 106. In one embodiment, the sealant delivery assembly 106 and the spray cap may include one or more structural features (e.g., swirl chambers) that are disclosed in commonly assigned U.S. Patent Application Publication No. 2021/0101162 to Trezza I I et al., the disclosure of which is hereby incorporated by reference herein.

Figures 13A, 13B:
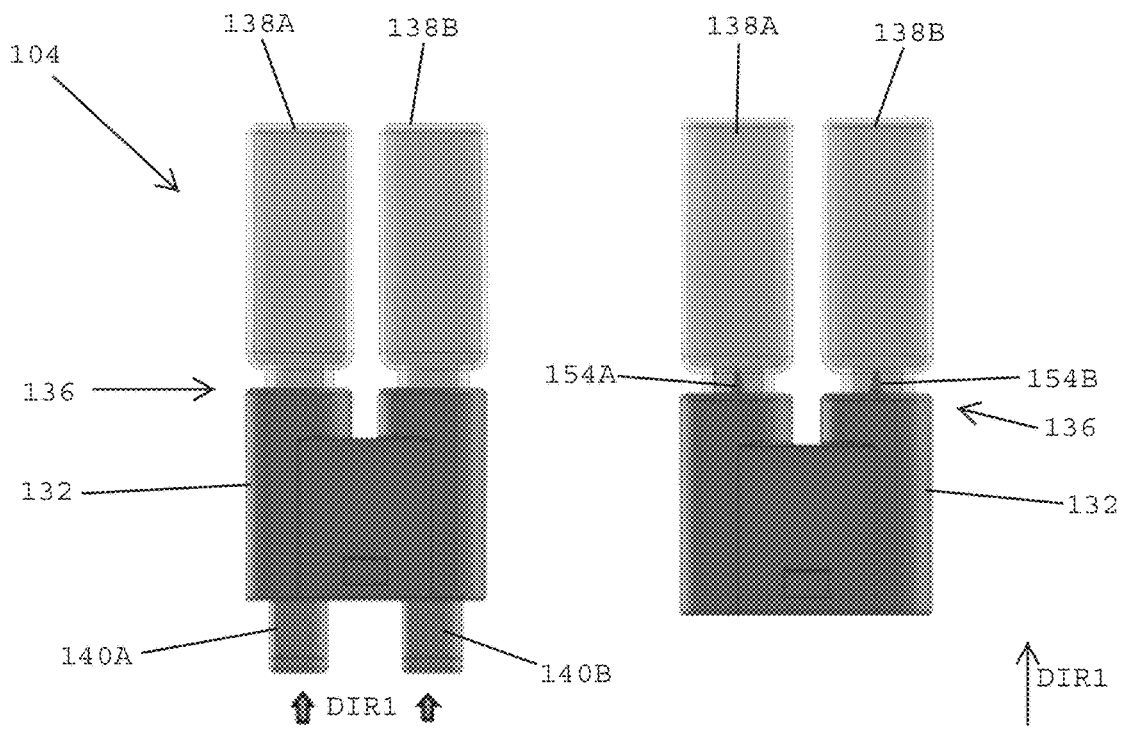
FIG. 13A shows a side view of the vial assembly of FIG. 8A with the first and second piercing elements in retracted positions.
FIG. 13B shows a side view of the vial assembly of FIG. 8B with the first and second piercing elements in extended positions.

Referring to FIG. 13A, in one embodiment, the vial assembly 104 includes the vial assembly housing 132 with the first and second vials 138A, 138B secured to the distal end 136 of the vial assembly housing 132. The first vial 138A contains a first reactive powder component (e.g., fibrinogen powder; a reactive synthetic powder; a cross-linker, etc.), and the second vial 138B contains a second reactive powder component (e.g., thrombin powder; a reactive synthetic powder; a crosslinker, etc.).

Referring to FIG. 13B, in one embodiment, the first and second piercing elements 140A, 140B may be advanced in the distal direction DIR1 toward the distal end 136 of the vial assembly housing 132 for moving the first and second piercing elements into the extended position shown in FIG. 8B, In the extended position, the first and second piercing spikes 154A, 154B of the respective first and second piercing elements pierce the respective first and second sealing membranes 148A, 148B (FIG. 8B) that seal the vial openings at the proximal ends of the respective first and second vials 138A, 138B.

Figure 14:
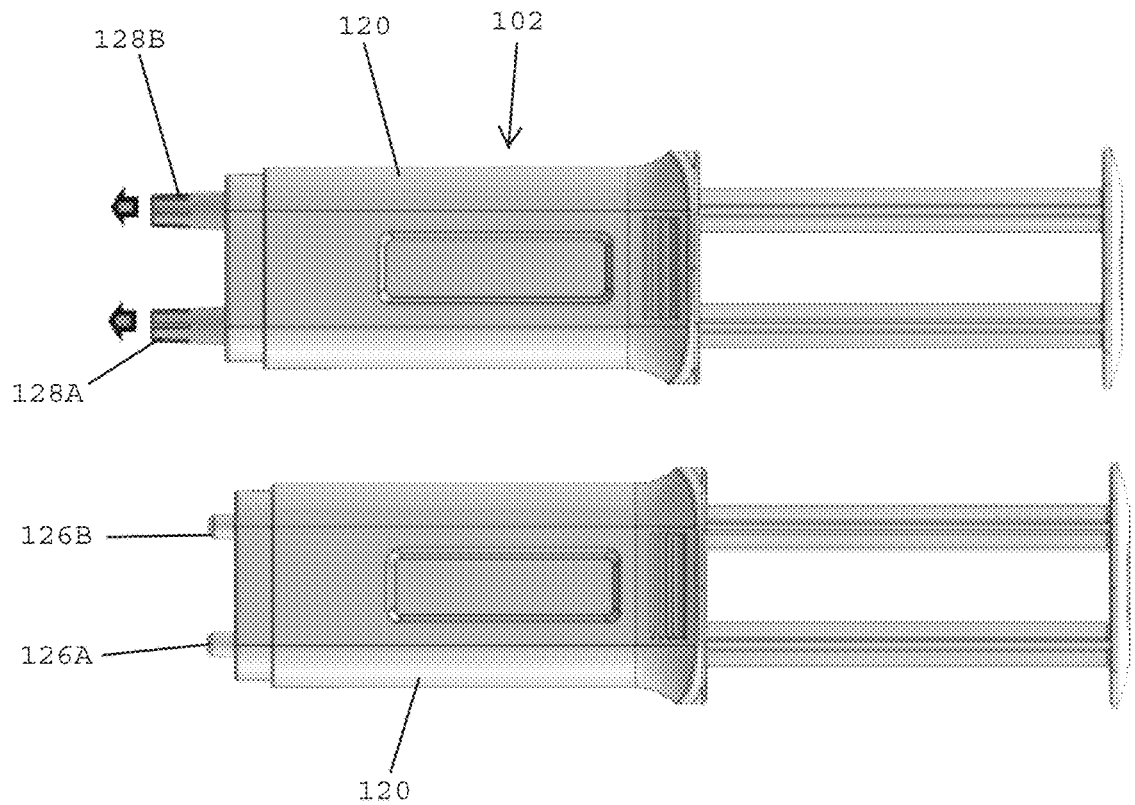
FIG. 14 shows a top view of the syringe assembly shown in FIG. 1.

Referring to FIG. 14, in one embodiment, the syringe assembly 102 that contains the first and second liquids that are used to reconstitute the reactive powder components may be prepared for being connected to a proximal end of the vial assembly housing 132 (FIG. 13B) by removing the first and second end caps 128A, 128B. Removing the first and second end caps 128A, 128B exposes the respective first and second dispensing tips 126A, 126B that are accessible at the distal end of the syringe assembly housing 120.

Figure 15A:
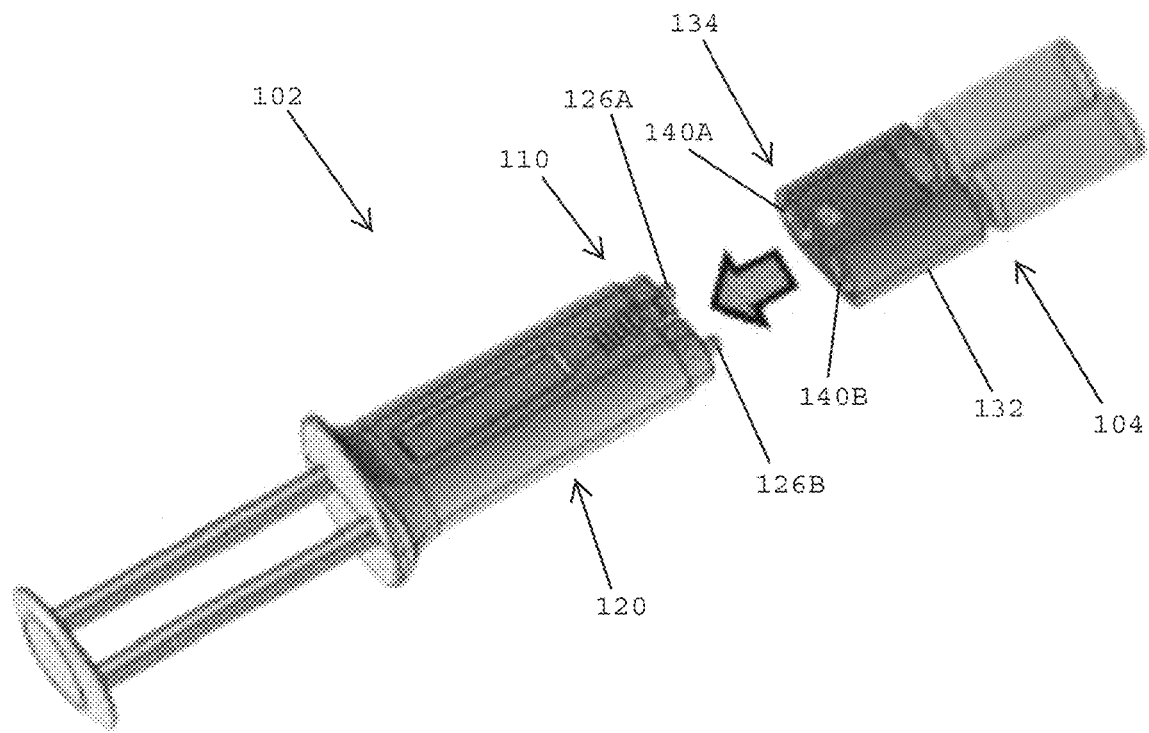
FIG. 15A shows a stage of a method of coupling a distal end of a syringe assembly with a proximal end of a vial assembly, in accordance with one embodiment of the present patent application.

Referring to FIG. 15A, in one embodiment, after the first and second end caps 128A, 128B (FIG. 14) have been removed from the distal end of the syringe assembly housing 120 of the syringe assembly 102; the distal end of the syringe assembly housing 120 is preferably coupled with the proximal end 134 of the vial assembly housing 132. The first dispensing tip 126A is preferably inserted into an opening at the proximal end of the first piercing element 140A and the second dispensing tip 126B is preferably inserted into an opening at the proximal end of the second piercing element 140B.

Figure 15B:
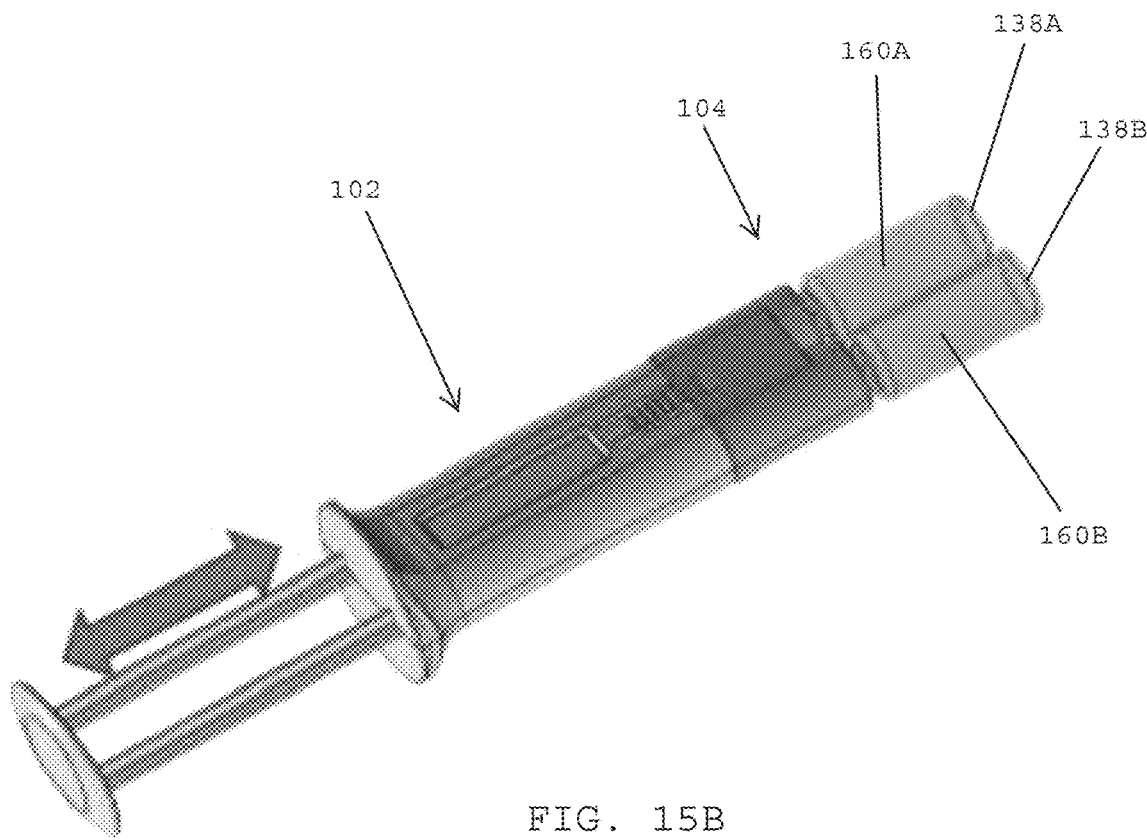
FIG. 15B shows the syringe assembly and the vial assembly of FIG. 15A after the distal end of the syringe assembly has been coupled with the proximal end of the vial assembly.

Referring to FIG. 15B, after the vial assembly 104 has been assembled with the distal end of the syringe assembly 102, the first liquid disposed within the first syringe 124A (FIG. 4A) of the syringe assembly is preferably in fluid communication with the first powder (e.g.; a powdered reactive component) disposed within the first powder chamber 160A of the first vial 138A. Similarly, the second liquid disposed within the second syringe 124B (FIG. 4A) of the syringe assembly is preferably in fluid communication with the second powder (e.g., powdered reactive component) disposed within the second powder chamber 160B of the second vial 138B.

Figure 15C:
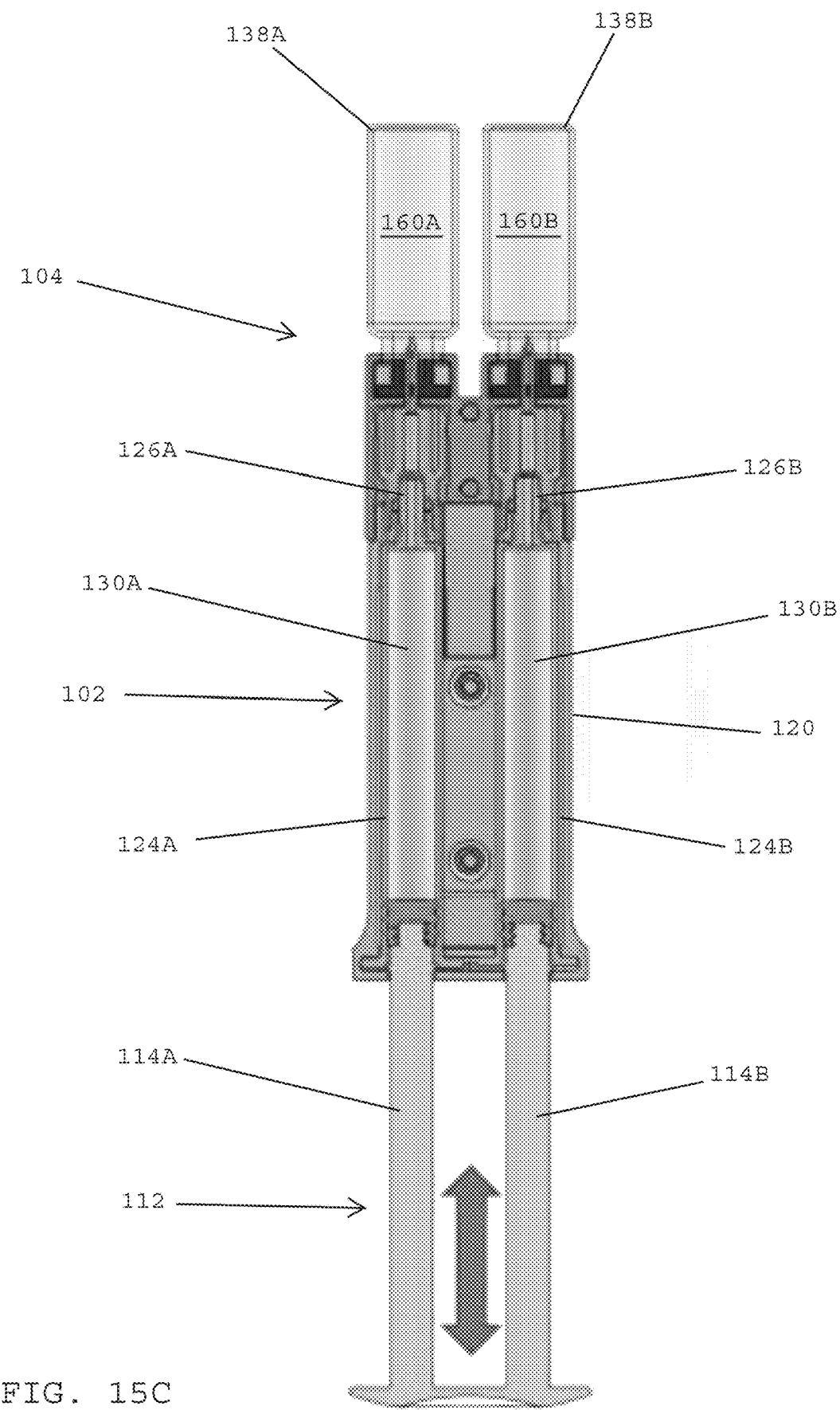
FIG. 15C shows a method of using the syringe assembly and the vial assembly of FIG. 15B for mixing a first liquid with a first powder and a second liquid with a second powder, in accordance with one embodiment of the present patent application.

FIG. 15C shows the distal end of the syringe assembly 102 connected with the proximal end of the vial assembly 104. The syringe assembly includes the first syringe 124A having a first fluid chamber 130A that contains a first activation fluid (e.g., a diluent; a buffer solution; a catalyst; an initiator; an activation fluid, etc. that activates the first powder). The syringe assembly 102 also desirably includes a second syringe barrel 124B having a second fluid chamber 130B that contains a second activation fluid (e.g.; a diluent; a buffer solution; a catalyst; an initiator; an activation fluid, etc. that activates the second powder). The first syringe barrel 124A is connected with the proximal end of the vial assembly 104 so that the first dispensing tip 128A of the first syringe barrel 124A is aligned with and in fluid communication with the first vial opening 146A of the first vial 138A. The first vial 138A has a first powder chamber 160A that contains a first powder, which will be reconstituted using the first activation fluid disposed within the first fluid chamber 130A of the first syringe barrel 124A. The second dispensing tip 128B at the distal end of the second syringe 124B is preferably in alignment with the second vial opening 146B of the second vial 138B. The second vial 138B preferably includes a second powder chamber 160B that contains a second powder, which will be reconstituted using the second activation fluid disposed within the second fluid chamber 130B of the second syringe 124B.

During the stage shown in FIG. 15C, the first liquid and the first powder remain isolated from the second liquid and the second powder.

In one embodiment, the first activation fluid within the first syringe 124A is mixed with the first powder in the first vial 138A by advancing and retracting the dual barrel plunger 112 in distal and proximal directions. As the first plunger rod 114A is advanced toward the distal end of the syringe housing 120, the first activation fluid within the first fluid chamber 130A of the first syringe 124A is forced into the first powder chamber 160A of the first vial 138A for reconstituting the first powder into a first therapeutic solution. Mien the first plunger rod 114A is retracted away from the distal end of the syringe housing 120, the first therapeutic solution of the first powder and the first activation fluid is drawn back into the first fluid chamber 130A of the first syringe 124A. The first plunger rod 114A may be repeatedly reciprocated back and forth between an extended position and a retracted position for thoroughly mixing the first activation fluid and the first powder to form the first precursor solution (e.g., a flowable liquid). In one embodiment, after the first precursor solution has been formed, the first plunger rod 114A is preferably fully retracted for drawing the entire volume of the first precursor solution into the first fluid chamber 130A of the first syringe 124A.

In one embodiment, the second activation fluid within the second syringe 124B is mixed with the second powder within the second vial 138B by advancing and retracting the dual barrel plunger 112 in distal and proximal directions. As the second plunger rod 114B is advanced toward the distal end of the syringe assembly housing 120, the second activation fluid within the second fluid chamber 130B of the second syringe 124B is forced into the second powder chamber 160B of the second vial 138B for reconstituting the second powder into a second therapeutic solution. When the second plunger rod 114B is retracted away from the distal end of the syringe assembly housing 120, the second therapeutic solution of the second powder and the second activation fluid is drawn back into the second fluid chamber 130B of the second syringe 124B. The second plunger rod 114B may be repeatedly reciprocated back and forth between an extended position and a retracted position for thoroughly mixing the second activation and the second powder to form the second precursor solution (e.g., a flowable liquid). In one embodiment, after the second precursor solution has been formed, the second plunger rod 114B is preferably fully retracted for drawing the entire volume of the second precursor solution into the second fluid chamber 130B of the second syringe 124B.

Figure 16:
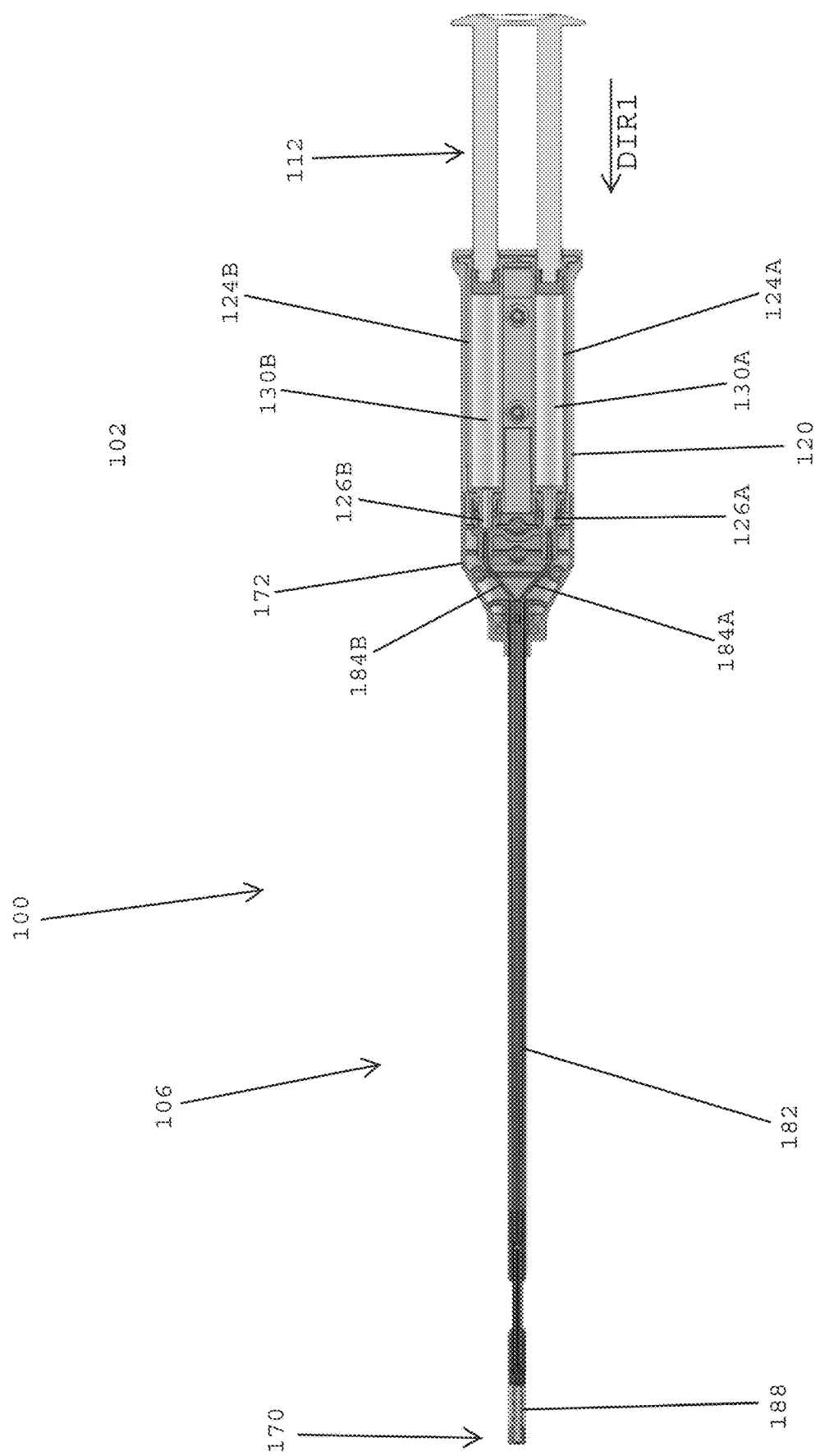
FIG. 16 is a cross-sectional view of a sealant applicator including the sealant delivery assembly of FIG. 9 secured to the distal end of the syringe assembly of FIG. 2, in accordance with one embodiment of the present patent application.

Referring to FIGS. 15C and 16, in one embodiment, after the first and second precursor solutions have been generated and drawn back into the first and second fluid chambers 130A, 180B of the respective first and second syringes 124A, 124B of the syringe assembly 102, the vial assembly 104 may be uncoupled from the distal end of the syringe assembly housing 120 and the sealant delivery assembly 106 may be secured to the distal end of the syringe assembly housing 120 for expressing the first and second precursor solutions from the distal end of the sealant applicator. In one embodiment, the sealant delivery assembly housing 172 at the proximal end of the sealant delivery assembly 106 is preferably connected with the distal end of the syringe assembly housing 120. The cannula 182 and the spray tip 188 preferably extend toward the distal end 170 of the sealant delivery assembly 106.

After the sealant delivery assembly has been secured to the distal end of the syringe assembly housing, the first fluid chamber 130A of the first syringe 124A that contains the first precursor is preferably in fluid communication with the spray tip 188 via the first flexible tube 184A. The second fluid chamber 130B of the second syringe 124B that contains the second precursor is preferably in fluid communication with the spray tip 188 via the second flexible tube 184B.

In one embodiment, the dual barrel plunger 112 is depressed in the distal direction designated DIR1 to force the first and second precursor solutions from the first and second fluid chambers 130A, 130B of the respective first and second syringes 124A, 124B, whereupon the first and second precursor solutions flow through the respective first and second flexible tubes 184A, 184B until they reach the spray tip 188. Upon reaching the spray tip, the first and second precursor solutions are mixed together by the static mixer 194 (FIG. 12), whereupon the first and second precursor solutions react with one another to form a tissue sealant or hemostat, which is expressed from the dispensing opening 196 of the spray cup 197 (FIG. 12) located at the distal end 170 of the sealant delivery assembly 106.

Figure 17:
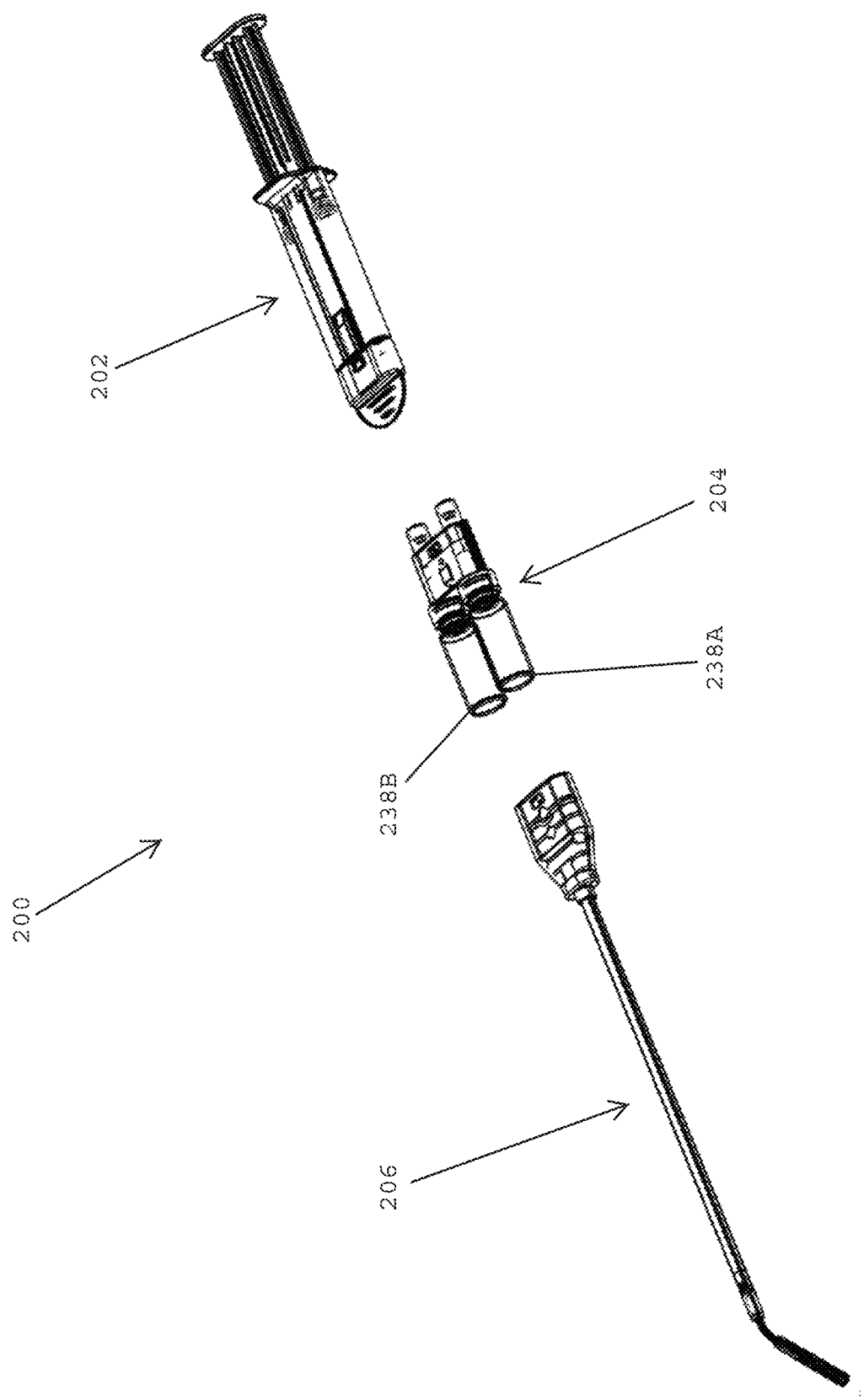
FIG. 17 is a perspective view of the components of a sealant delivery system including a syringe assembly, a vial assembly, and a sealant delivery system having a spray tip, in accordance with one embodiment of the present patent application.

Referring to FIG. 17, in one embodiment, a sealant delivery system 200 preferably includes a syringe assembly 202 that contains one or more liquids or fluids for reconstituting therapeutic powders, a vial assembly 204 having first and second vials 238A, 238B containing powdered reactive components, and a sealant delivery assembly 206 for expressing a sealant or hemostat. In one embodiment, the syringe assembly 202 may be a molded component having side-by-side double barrel cavities that are configured for holding the liquids that are used for reconstituting the reactive powdered components. In one embodiment, the vial assembly 204 may be similar to the vial assembly 104 disclosed above in the embodiments shown in FIGS. 5A-58, 6, 7, and 8A-88. In one embodiment, the sealant delivery assembly 206 may be similar to the sealant delivery assembly 106 shown and described above in FIGS. 9-12.

Figure 18:
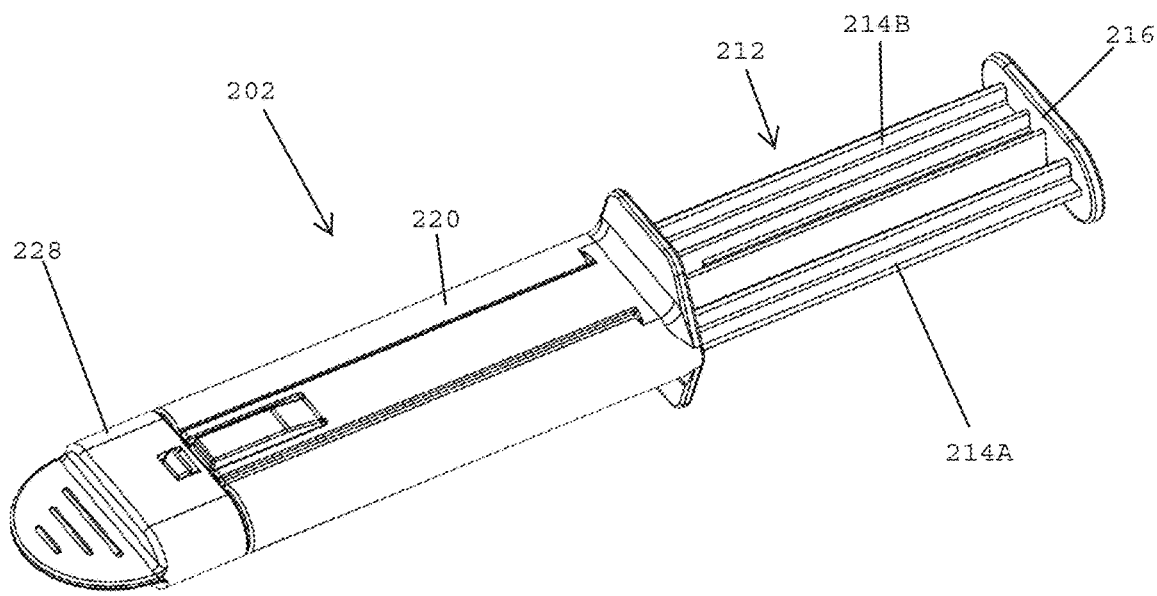
FIG. 18 is a perspective view of the syringe assembly shown in FIG. 17.

Referring to FIG. 18, in one embodiment, the syringe assembly 202 preferably includes a syringe assembly housing 220 that is adapted to receive the distal end of a dual barrel plunger 212. The dual barrel plunger 212 preferably includes a first plunger rod 214A that is insertable into a first syringe barrel cavity formed in the syringe assembly housing 220 of the syringe assembly 202 and a second plunger rod 214B that is insertable into a second syringe barrel cavity of the syringe assembly housing 220 of the syringe assembly 202. In one embodiment, the proximal ends of the first and second syringe plunger rods 214A, 214B are interconnected by a thumb tab 216 that defines a proximal end of the dual barrel plunger 212.

In one embodiment, the syringe assembly 202 preferably includes a syringe end cap 228 that is releasably secured to the distal end of the syringe assembly housing 220 of the syringe assembly 202 for covering syringe dispensing tips that are in fluid communication with the respective syringe barrel cavities formed in the syringe assembly housing 220, as will be described in more detail herein.

Figure 19:
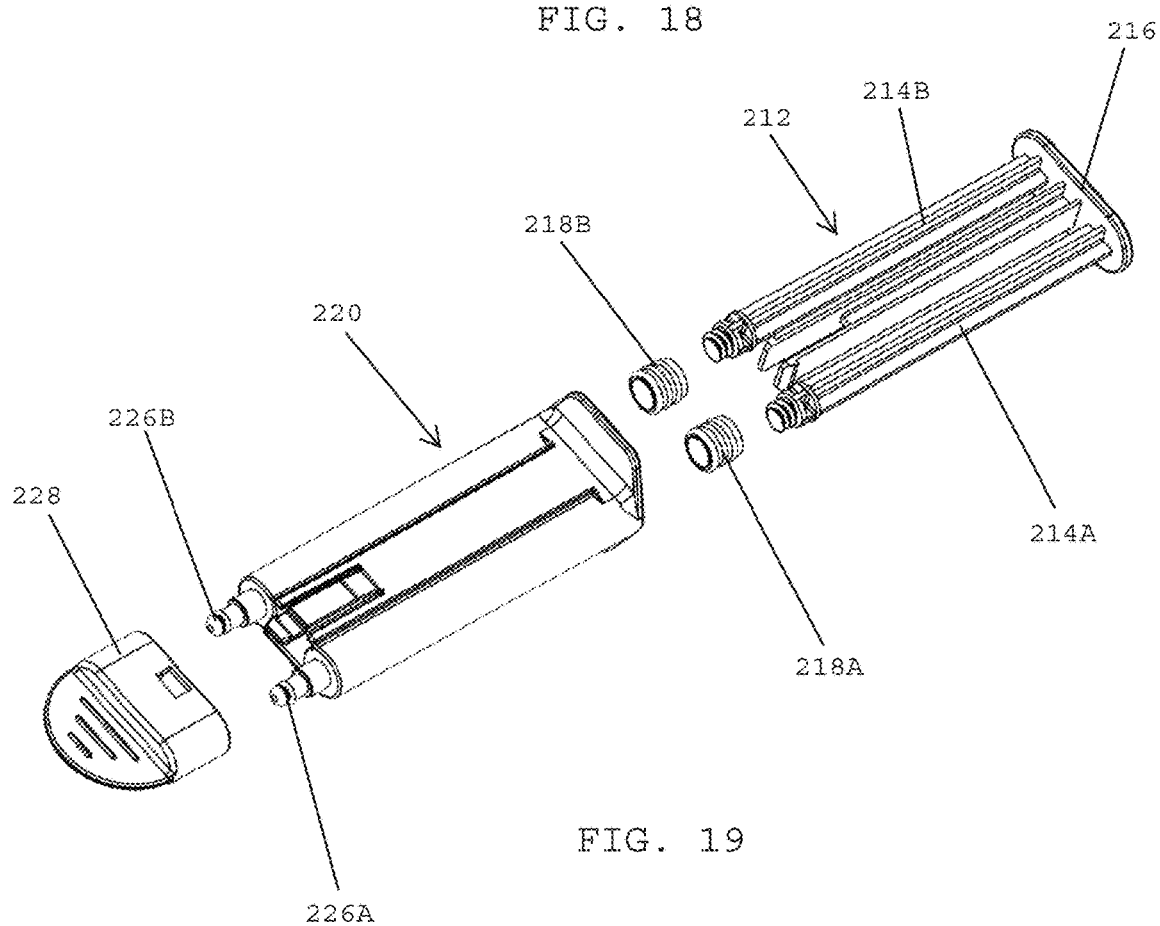
FIG. 19 is an exploded view of the syringe assembly shown in FIG. 18.

Referring to FIG. 19, the syringe assembly 202 preferably includes the syringe assembly housing 220 having a proximal end that is adapted to receive the dual barrel plunger 212 and a distal end that is adapted to be connected with the syringe end cap 228. The syringe assembly housing 220 preferably includes a first dispensing tip 226A that projects from a distal end of the syringe housing 220 and that is in fluid communication with a first fluid chamber of a first syringe barrel cavity that is integrally formed within the syringe assembly housing 220. The syringe assembly housing 220 preferably includes a second dispensing tip 226B that projects from a distal end of the syringe housing 220 and that is in fluid communication with a second fluid chamber of a second syringe barrel cavity that is integrally formed within the syringe assembly housing 220.

In one embodiment, the syringe end cap 228 may be disconnected from the distal end of the syringe assembly housing 220 for exposing the first and second dispensing tips 226A, 226B. After the syringe end cap 228 has been removed for exposing the dispensing tips 226A, 226B, the distal end of the syringe assembly housing may be assembled with a vial assembly or a sealant delivery assembly.

In one embodiment, the double barrel plunger 212 preferably includes a first plunger rod 214A having a distal end that is adapted to be connected with a first plunger 218A. The double barrel plunger 212 also includes a second plunger rod 214B having a distal end that is adapted to be connected with a second plunger 218B. In one embodiment, the distal end of the first plunger rod 214A with the first plunger 218A secured thereto is insertable into the first fluid chamber defined by the first syringe barrel cavity of the syringe assembly housing and the distal end of the second plunger rod 214B with the second plunger 218B secured thereto is inserted into the second fluid chamber defined by the second syringe barrel cavity of the syringe assembly housing.

Figure 20:
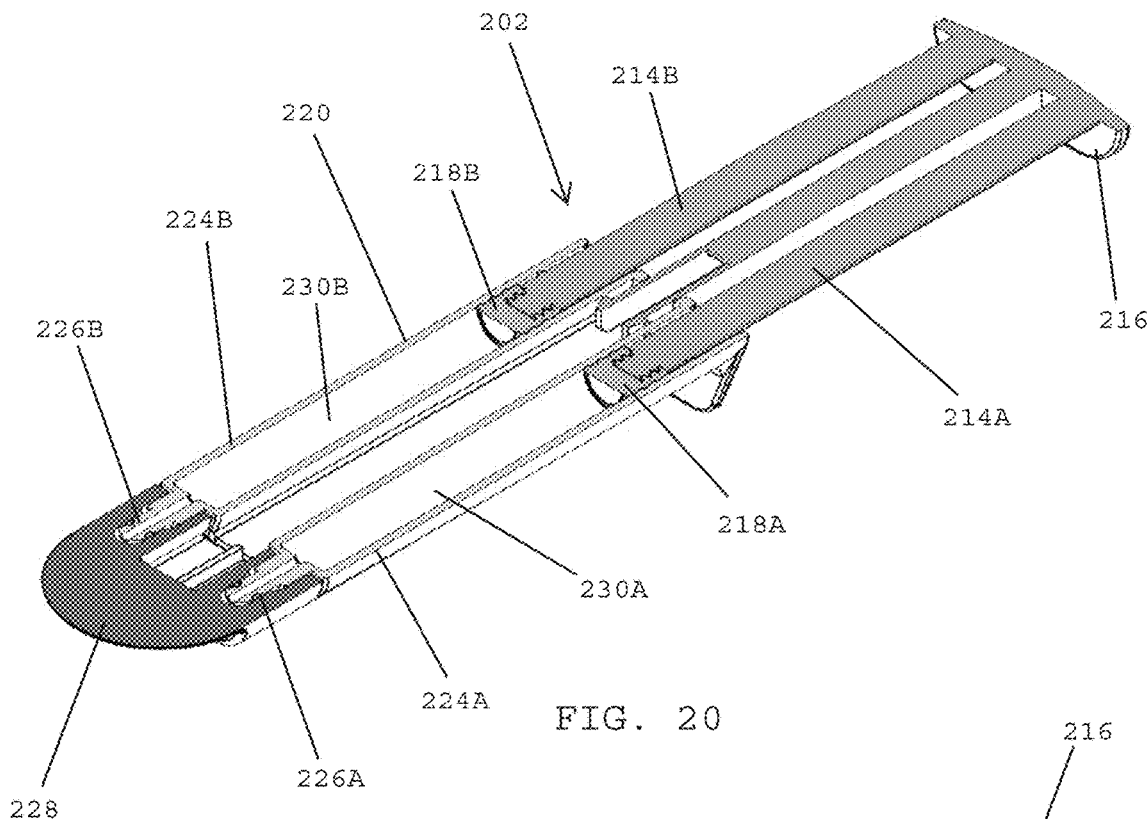
FIG. 20 is a perspective, cross-sectional view of the syringe assembly shown in FIG. 18, the syringe assembly having an end cap secured to a distal end of a syringe assembly housing, in accordance with one embodiment of the present patent application.

Referring to FIG. 20, in one embodiment, the first plunger 218A and distal end of the first plunger rod 214A are inserted into the first fluid chamber 230A of the first syringe barrel cavity 224A that is integrally formed in the syringe assembly housing 220 of the syringe assembly 202. In a similar manner, the second plunger 218B and the distal end of the second plunger rod 214B are inserted into the second fluid chamber 230B of the second syringe barrel cavity that is integrally formed in the syringe assembly housing 220 of the syringe assembly 202. In one embodiment, a first liquid (e.g., a diluent; a buffer solution; a catalyst; an initiator; an activation fluid; etc.) is disposed within the first fluid chamber 230A of the first syringe barrel cavity 224B. In one embodiment, a second liquid (e.g., a diluent; a buffer solution; a catalyst; an initiator; an activation fluid, etc.) is disposed within the second fluid chamber 230B of the second syringe barrel cavity 224B, The first and second activation fluids may have the same or different properties.

In one embodiment, during storage, the syringe assembly end cap 228 is preferably connected with the distal end of the syringe assembly housing 220 of the syringe assembly 202 for covering the first and second dispensing tips 226A, 228B that are in fluid communication with the respective first and second fluid chambers 230A, 230B.

Figure 21:
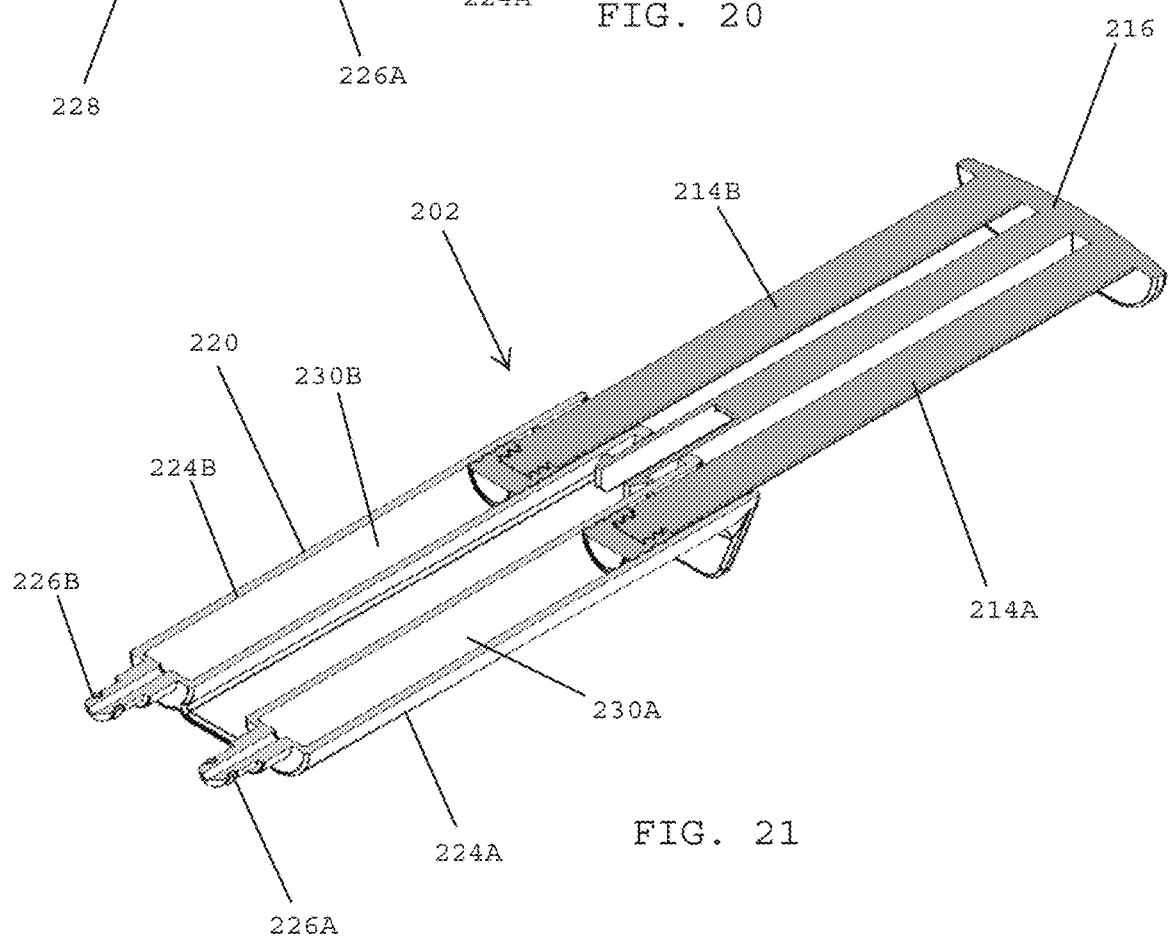
FIG. 21 shows the perspective, cross-sectional view of the syringe assembly shown in FIG. 20 after the end cap has been removed for uncovering the distal end of the syringe assembly housing.

Referring to FIG. 21, in one embodiment, the syringe assembly end cap 228 (FIG. 20) may be removed from the distal end of the syringe assembly housing 220 for uncovering the syringe dispensing tips 226A, 226B that are in fluid communication with the first and second fluid chambers 230A, 236B of the respective first and second syringe barrels cavities 224A, 224B.

Figure 22A:
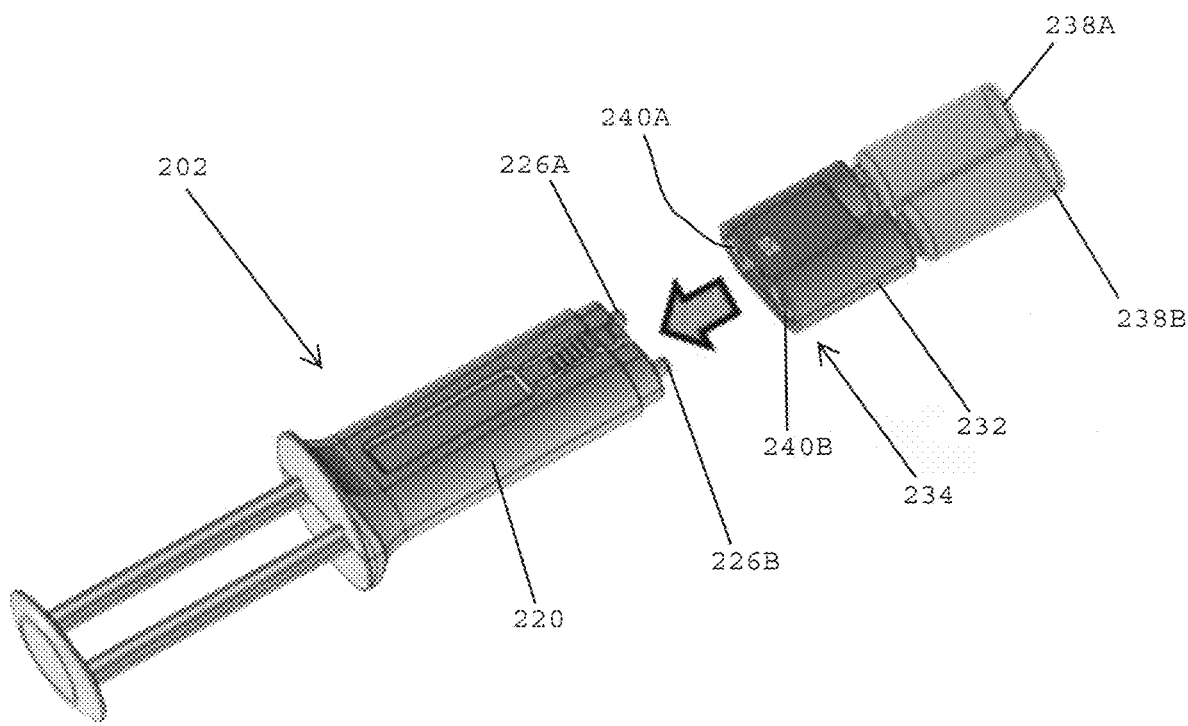
FIG. 22A shows a stage of a method of coupling a distal end of the syringe assembly of FIG. 18 with a proximal end of the vial assembly of FIG. 17, in accordance with one embodiment of the present patent application.

Referring to FIG. 22A, in one embodiment, after the syringe end cap 228 (FIG. 20) has been removed from the distal end of the syringe assembly housing 220 of the syringe assembly 202, the distal end of the syringe assembly housing 220 may be coupled with a proximal end 234 of a vial assembly housing 232 of the vial assembly 204. The first syringe dispensing tip 226A is preferably inserted into an opening at the proximal end of a first piercing element 240A for providing fluid communication between the first fluid chamber 230A (FIG. 21) and the first vial 238A. The second syringe dispensing tip 226B is preferably inserted into an opening at the proximal end of a second piercing element 240B for providing fluid communication between the second fluid chamber 230B (FIG. 21) and the second vial 238B.

Figure 22B:
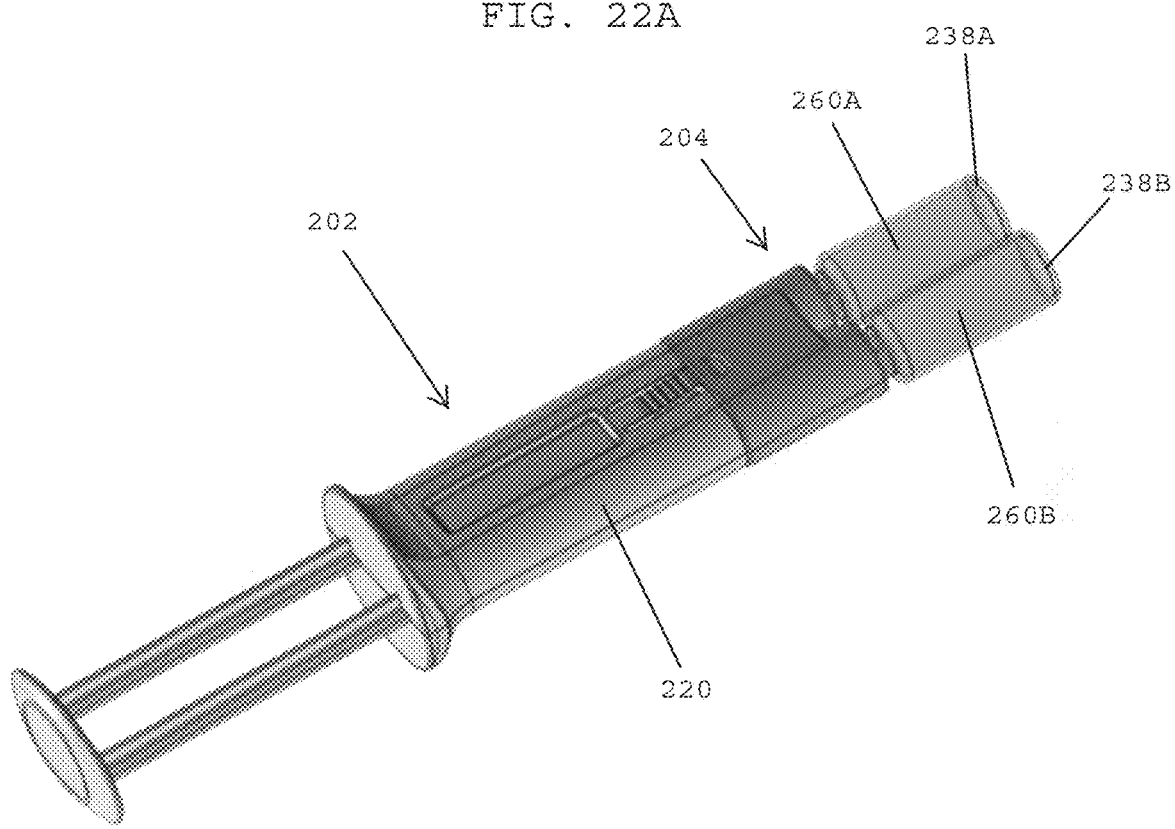
FIG. 22B shows the syringe assembly and the vial assembly of FIG. 22A after the distal end of the syringe assembly has been coupled with the proximal end of the vial assembly.

Referring to FIG. 22B, after the vial assembly 204 has been assembled with the distal end of the syringe assembly housing 220 of the syringe assembly 202, the first liquid (e.g., a diluent; a buffer solution; a catalyst; an initiator; an activation fluid; a reconstitution fluid, etc.) disposed within the first fluid chamber 230A of the first syringe barrel cavity 224A (FIG. 21) of the syringe assembly housing 220 of the syringe assembly 202 is preferably in fluid communication with the first powder disposed within a first powder chamber 260A of a first vial 238A of the vial assembly 204. Similarly, the second liquid (e.g., a diluent; a buffer solution; a catalyst; an initiator; an activation fluid; a reconstitution fluid, etc.) disposed within the second fluid chamber 230B of the second syringe barrel cavity 224B (FIG. 21) of the syringe assembly housing 220 of the syringe assembly 202 is preferably in fluid communication with the second powder disposed within a second powder chamber 268B of a second vial 238B of the vial assembly 204.

Figure 22C:
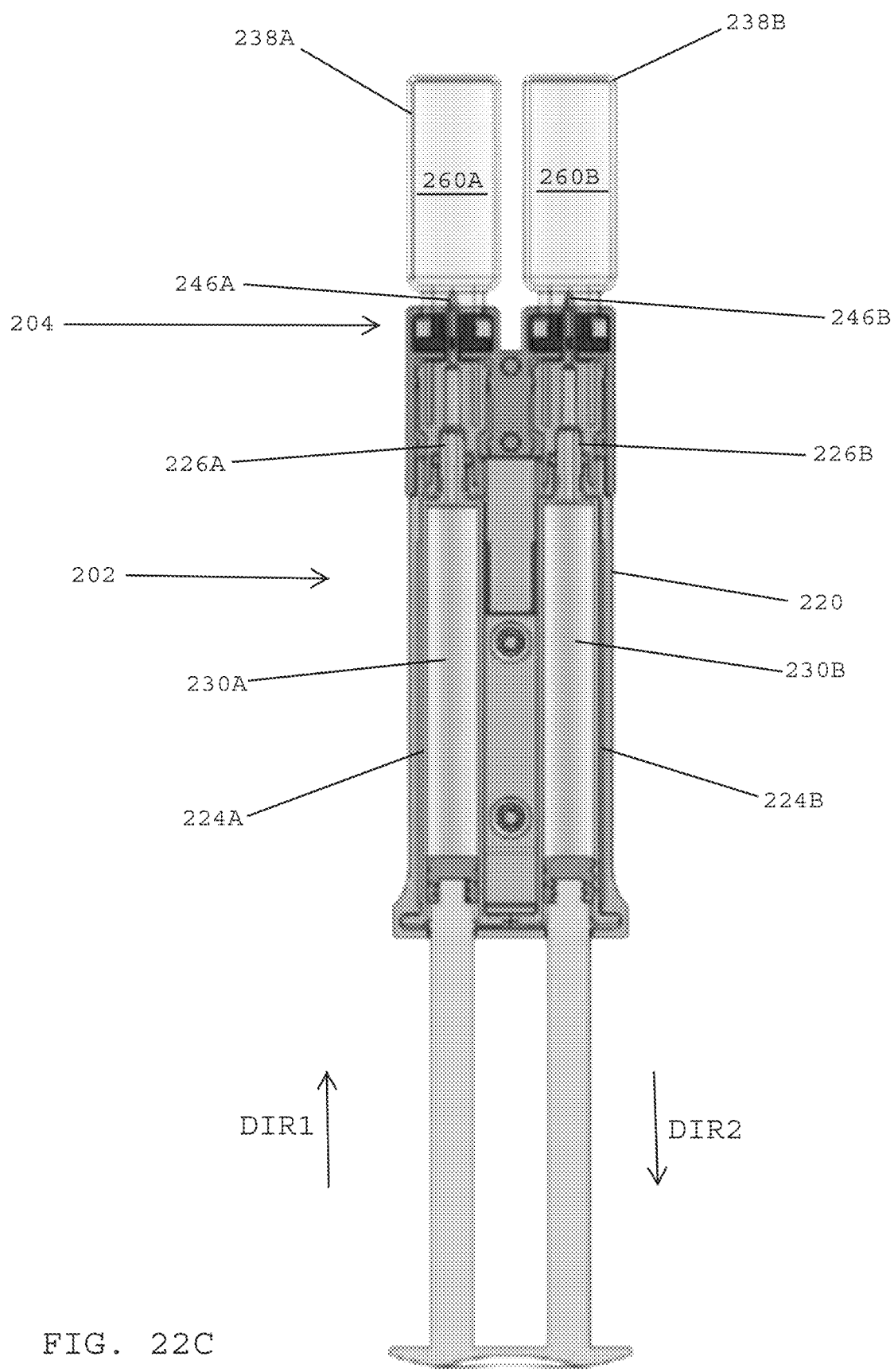
FIG. 22C shows a method of using the syringe assembly and the vial assembly of FIG. 22B for mixing a first liquid with a first powder and a second liquid with a second powder, in accordance with one embodiment of the present patent application.

Referring to FIG. 22C, in one embodiment, the distal end of the syringe assembly 202 is connected with the proximal end of the vial assembly 204. The syringe assembly includes the first syringe barrel cavity 224A having a first fluid chamber 230A that contains the first liquid for reconstitution the first powder. The first syringe barrel cavity 224A is connected with the proximal end of the vial assembly 204 so that the first dispensing tip 226A of the first syringe barrel cavity 224A is aligned with and in fluid communication with the first vial opening 246A of the first vial 238A. The first vial 238A has a first powder chamber 260A that contains a first powder, which will be reconstituted using the first liquid that is disposed within the first fluid chamber 230A of the first syringe barrel cavity 224A.

In one embodiment, the syringe assembly 202 desirably includes the second syringe barrel cavity 224B having a second fluid chamber 230B that contains a second liquid that is used for reconstituting the second powder. The second dispensing tip 2268 at the distal end of the second syringe barrel cavity 224B is preferably in alignment with the second vial opening 246B of the second vial 238B. The second vial 238B preferably includes a second powder chamber 260B that contains a second powder, which will be reconstituted using the second liquid disposed within the second fluid chamber 230B of the second syringe barrel cavity 224B.

In one embodiment, by advancing and retracting the dual barrel plunger 112 in distal direction DIR1 and the proximal direction DIR2, the first liquid within the first fluid chamber 230A of the first syringe barrel cavity 224A is mixed with the first powder disposed within the first powder compartment 260A of the first vial 138A. As the first plunger rod 114A is advanced distally in the direction DIR1 toward the distal end of the syringe assembly housing 220, the first liquid within the first fluid chamber 230A of the first syringe barrel cavity 224A is forced into the first powder chamber 260A of the first vial 238A. When the first plunger rod 214A is retracted away from the distal end of the syringe assembly housing 220, a first precursor solution including the first powder and first liquid is drawn back into the first fluid chamber 230A of the first syringe barrel cavity 224A. The first plunger rod 214A may be repeatedly reciprocated back and forth between an extended position and a retracted position for thoroughly mixing the first liquid and the first powder component to form the first precursor solution (e.g., a flowable liquid). In one embodiment, after the first precursor solution has been generated, the first plunger rod 214A is preferably fully retracted for drawing the entire volume of the first precursor solution back into the first fluid chamber 230A of the first syringe barrel cavity 224A.

In one embodiment, the second liquid contained within the second syringe barrel cavity 224B may be mixed with the second powder disposed within the second powder component 260B of the second vial 138B by advancing and retracting the dual barrel plunger 112 in distal (DIR1) and proximal (DIR2) directions. As the second plunger rod 114B is advanced toward the distal end of the syringe assembly housing 220, the second liquid within the second fluid chamber 230B of the second syringe barrel cavity 224B is forced into the second powder chamber 260B of the second vial 2388 for reconstituting the second powder into a second precursor solution. When the second plunger rod 214B is retracted away from the distal end of the syringe assembly housing 220, the second precursor solution including the second powder and the second liquid is drawn back into the second fluid chamber 230B of the second syringe barrel cavity 224B. The second plunger rod 214B may be repeatedly reciprocated back and forth between an extended position and a retracted position for thoroughly mixing the second liquid and the second powder to form the second precursor solution (e.g., a flowable liquid). In one embodiment, after the second precursor solution has been formed, the second plunger rod 214B is preferably fully retracted for drawing the entire volume of the second precursor solution back into the second fluid chamber 230B of the second syringe barrel cavity 224B.

In one embodiment, the first and second precursor solutions may be mixed together to form a tissue sealant or hemostat that is applied on tissue during a surgical procedure, such as a minimally invasive surgical procedure.

Referring to FIGS. 22C, 23A-23B, and 24, in one embodiment, after the first and second precursor solutions have been generated and drawn back into the first and second fluid chambers 230A, 230B of the respective first and second syringe barrel cavities 224A, 224B, the vial assembly 204 (FIG. 22C) may be uncoupled from the distal end of the syringe assembly housing 220 for exposing the first and second dispensing tips 226A, 226B (FIG. 22C). In one embodiment, the sealant delivery assembly housing 272 at the proximal end of the sealant delivery assembly 206 is preferably coupled with the distal end of the syringe assembly housing 220. The cannula 282 and the spray tip 288 preferably extend toward the distal end 270 of the sealant delivery assembly 206.

After the sealant delivery assembly 206 has been secured to the distal end of the syringe assembly housing 220, the first fluid chamber 230A of the first syringe barrel cavity 224A that contains the first precursor solution is preferably in fluid communication with the spray tip 288 via a first fluid pathway (e.g., the first flexible tube 184A shown in FIG. 11). The second fluid chamber 200B of the second syringe barrel cavity 224B that contains the second precursor solution is preferably in fluid communication with the spray tip 288 via a second fluid pathway (e.g., the second flexible tube 1848 shown in FIG. 11).

Figure 23A:
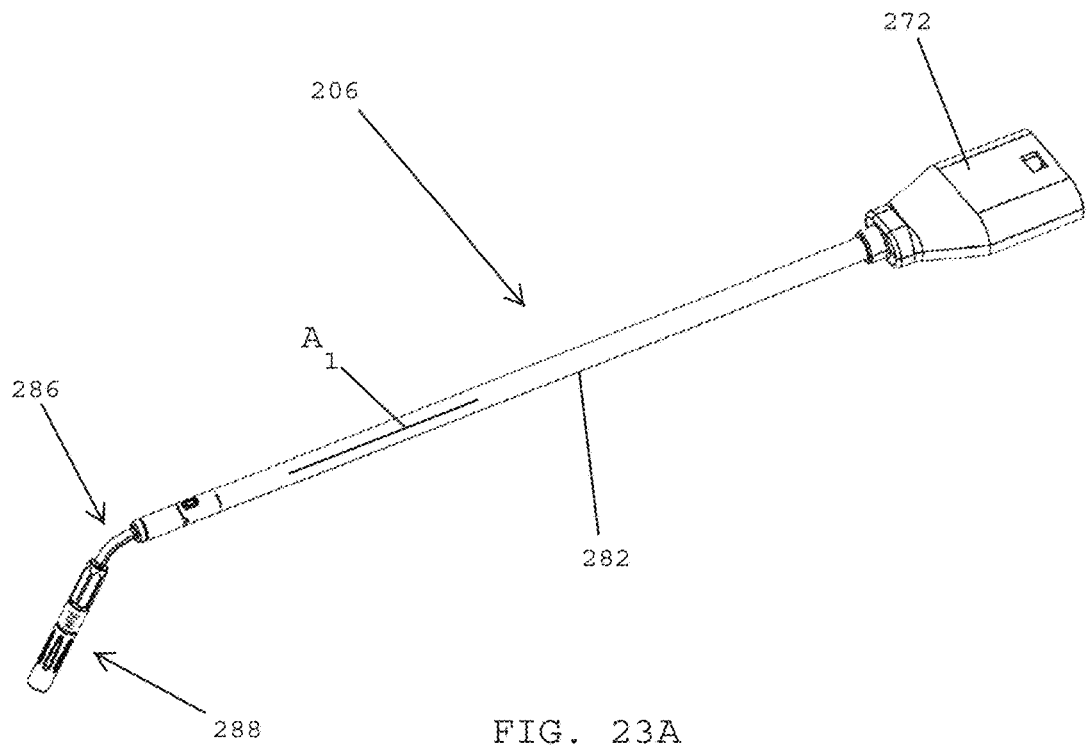
FIG. 23A is a perspective view of the sealant delivery assembly shown in FIG. 17.
Figure 23B:
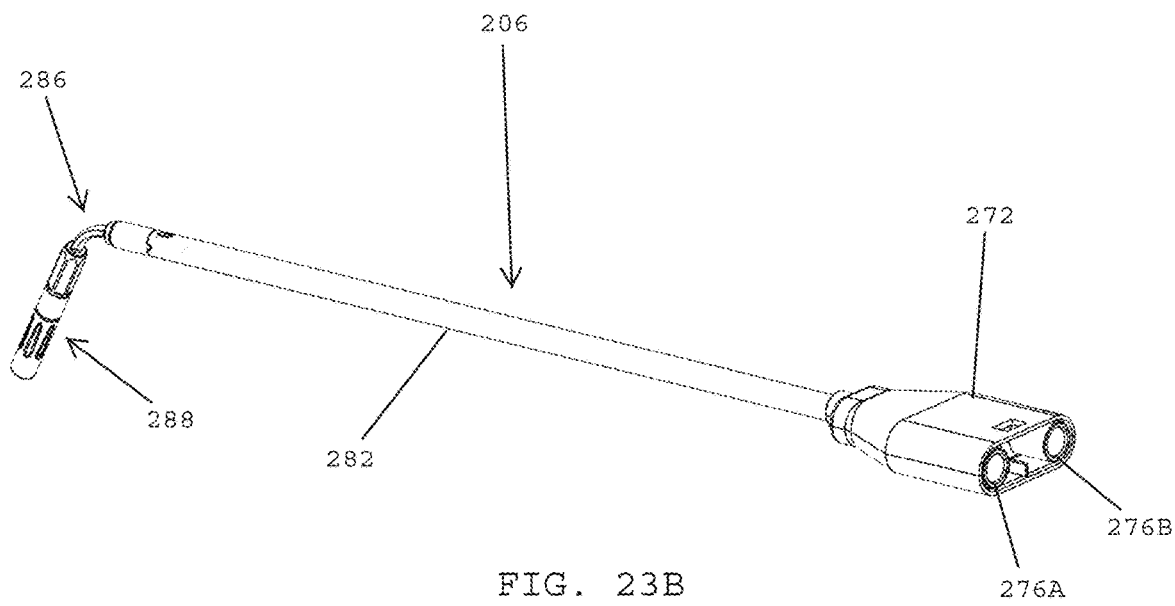
FIG. 23B is a perspective view of a proximal end of the sealant delivery assembly shown in FIG. 23A.

Referring to FIGS. 23A and 23B, in one embodiment, the sealant delivery assembly 206, similar to that shown and described above in FIGS. 9 and 10, preferably includes an elongated cannula 282 having a proximal end and a distal end. A sealant delivery assembly housing 272 is secured to the proximal end of the cannula 282, and spray tip 288 is secured to a distal end of the cannula 282 via a malleable connector 286. The malleable connector 286 desirably enables the spray tip 282 to be articulated to different angles relative to the longitudinal axis $A_1$ of the elongated cannula 282. The malleable connector may include a malleable rod or pin that maintains its shape after being bent into a particular orientation, which, in turn, holds the spray tip 282 in a selected orientation relative to the elongated axis $A_1$ of the cannula 282 (FIG. 24)

Figure 24:
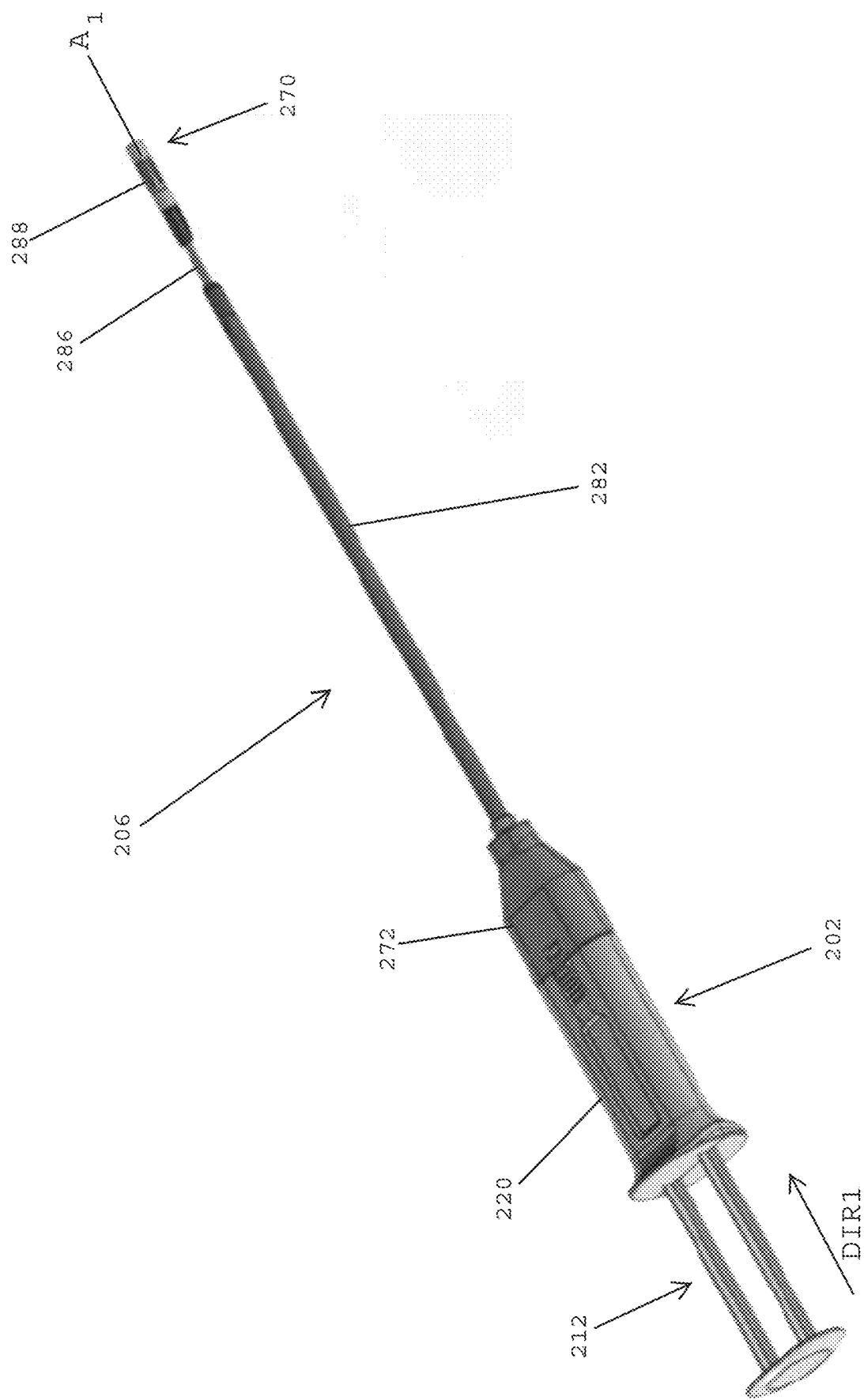
FIG. 24 is a perspective view of a sealant applicator including the sealant delivery assembly of FIGS. 23A and 23B and the syringe assembly of FIG. 21.

Referring to FIGS. 23B and 24, in one embodiment, the proximal end of the sealant delivery assembly housing 272 of the sealant delivery assembly 206 is connected with the distal end of the syringe assembly housing 220 of the syringe assembly 202. In one embodiment, the first dispensing tip 226A (FIG. 220) at the distal end of the syringe assembly housing 220 of the syringe assembly 202 is inserted into the first hub 276A at the proximal end of the sealant delivery assembly housing 272. The second dispensing tip 2268 (FIG. 22C) at the distal end of the syringe assembly housing 220 is inserted into the second hub 276B at the proximal end of the sealant delivery assembly housing 272.

In one embodiment, the spray tip 288 is coupled with the distal end of the cannula 282 by the malleable connector 286. The malleable connector 286 enables the spray tip 288 to be positioned at different angles relative to the longitudinal axis $A_1$ of the elongated cannula 282 of the sealant delivery assembly 206.

Referring to FIG. 24, in one embodiment, the distal end of the sealant delivery assembly 206 may have a similar construction as that shown and described above for the embodiment shown in FIG. 12. The malleable connector 286 couples the spray tip 288 to the distal end of the cannula 282. The malleable connector 286 preferably includes an elongated malleable component (e.g., the malleable metal rod 190 shown in FIG. 12) that extends along the length thereof. The malleable component enables the spray tip 288 to be positioned at different angles relative to the longitudinal axis $A_1$ of the cannula 282.

In one embodiment, the dual barrel plunger 212 is depressed in the distal direction designated DIR1 to force the first and second precursor solutions from the first and second fluid chambers 230A, 230B of the respective first and second syringe barrel cavities 224A, 224B (FIG. 22C), whereupon the first and second precursor solutions flow toward the spray tip 288 for being mixed together within the spray tip and expressed from the distal end 270 of the sealant delivery assembly 206.

In one embodiment, the sealant delivery system maintains the first and second precursor solutions isolated from one another until they are mixed together within the spray tip 288. Upon being mixed together within the spray tip 288, the first and second precursor solutions preferably react with one another to form a sealant or hemostat that controls bleeding. The sealant or hemostat is preferably sprayed onto tissue in fluid form, whereupon the interacting first and second precursor solutions cure, coagulate and/or gel to stop or control bleeding.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fail within the scope of the present invention.

What is claimed is:

1. A sealant delivery system comprising:
    a syringe assembly including side-by-side first and second syringes, said first syringe having a first fluid chamber and said second syringe having a second fluid chamber;
    a vial assembly coupled to a distal end of said syringe assembly, said vial assembly including side-by-side first and second vials;

said first vial having a proximal end that is aligned with a distal end of said first syringe, said first vial including a first vial opening at the proximal end thereof that is closed by a first sealing membrane;

said second vial having a proximal end that is aligned with a distal end of said second syringe, said second vial including a second vial opening at the proximal end thereof that is closed by a second sealing membrane;

said vial assembly including a first piercing element located between the distal end of said first syringe and the proximal end of said first vial, said first piercing element having a first piercing spike projecting from a distal end thereof, said first piercing element being moveable between a retracted position in which said first piercing spike is located on a proximal side of said first sealing membrane and an extended position in which said first piercing spike passes through said first sealing element for piercing said first sealing membrane to provide first fluid communication between said first fluid chamber of said first syringe and said first vial; and said vial assembly including a second piercing element located between the distal end of said second syringe and the proximal end of said second vial, said second piercing element having a second piercing spike projecting from a distal end thereof, said second piercing element being moveable between a retracted position in which said second piercing spike is located on a proximal side of said second sealing membrane and an extended position in which said second piercing spike passes through said second sealing element for piercing said second sealing membrane to provide second fluid communication between said second fluid chamber of said second syringe and said second vial.

2. The sealant delivery system as claimed in claim 1, further comprising:
said first piercing element defines a first fluid pathway extending along a length thereof for providing the first fluid communication between said first fluid chamber of said first syringe and said first vial; and
said second piercing element defines a second fluid pathway extending along a length thereof for providing the second fluid communication between said second fluid chamber of said second syringe and said second vial.

3. The sealant delivery system as claimed in claim 2, wherein said first and second fluid pathways are isolated from one another, and wherein said syringe assembly and said vial assembly may only be connected together in one configuration for ensuring that said first syringe is always matched with said first vial and said second syringe is always matched with said second vial.

4. The sealant delivery system as claimed in claim 1, further comprising: a first liquid disposed within said first fluid chamber of said first syringe;
a first powdered reactive component disposed within said first vial, wherein said first liquid and said first powdered reactive component are configured for being mixed together for reconstituting said first powdered reactive component to form a first therapeutic solution;
a second liquid disposed within said second fluid chamber of said second syringe;
a second powdered reactive component disposed within said second vial, wherein said second liquid and said second powdered reactive component are configured for being mixed together for reconstituting said second powdered reactive component to form a second therapeutic solution.

5. The sealant delivery system as claimed in claim 4, wherein said syringe assembly further comprises:
a dual barrel plunger including a first plunger rod inserted into a proximal end of said first syringe and a second plunger rod inserted into a proximal end of said second syringe;
a thumb tab interconnecting proximal ends of said first and second plunger rods;
said dual barrel plunger being moveable toward a distal end of said syringe assembly for forcing said first liquid into said first vial and forcing said second liquid into said second vial.

6. The sealant delivery system as claimed in claim 1, wherein the sealant delivery system further comprises a vial housing, and said vial housing further comprises:
a first guide channel extending between a proximal end and a distal end of said vial housing, wherein said first piercing element is disposed in said first guide channel and is configured for moving between the retracted position and the extended position;
a second guide channel extending between the proximal end and the distal end of said vial housing, wherein said second piercing element is disposed in said second guide channel and is configured for moving between the retracted position and the extended position.

7. The sealant delivery system as claimed in claim 6, wherein said vial housing further comprises:
a first proximal projection extending into said first guide channel that is adapted to contact said first piercing element for holding said first piercing element in the retracted position;
a first distal projection extending into said first guide channel that is adapted to contact said first piercing element for holding said first piercing element in the extended position;
a second proximal projection extending into said second guide channel that is adapted to contact said second piercing element for holding said second piercing element in the retracted position;
a second distal projection extending into said first guide channel that is adapted to contact said first piercing element for holding said first piercing element in the extended position.

8. The sealant delivery system as claimed in claim 7, further comprising:
said first piercing element including a first resilient flange adapted to sequentially engage said first proximal projection and said first distal projection of said vial housing when moving said first piercing element within said first guide channel from the retracted position to the extended position;
said second piercing element including a second resilient flange adapted to sequentially engage said second proximal projection and said second distal projection of said vial housing when moving said second piercing element within said second guide channel from the retracted position to the extended position.

9. The sealant delivery system as claimed in claim 1, further comprising:
said first piercing element having a central opening at a proximal end thereof;
said first syringe having a first dispensing tip projecting from the distal end thereof that is inserted into the central opening at the proximal end of said first piercing element;
said second piercing element having a central opening at a proximal end thereof;

said second syringe having a second dispensing tip projecting from the distal end thereof that is inserted into the central opening at the proximal end of said second piercing element.

10. A sealant delivery system comprising:

a syringe assembly including side-by-side first and second syringes, said first syringe having a first fluid chamber containing a first liquid and said second syringe having a second fluid chamber containing a second fluid;

a vial assembly coupled to a distal end of said syringe assembly, said vial assembly including side-by-side first and second vials;

said first vial containing a first powdered reactive component, said first vial having a proximal end that is aligned with a distal end of said first syringe and a first vial opening at the proximal end thereof that is closed by a first sealing membrane;

said second vial containing a second powdered component, said second vial having a proximal end that is aligned with a distal end of said second syringe and a second vial opening at the proximal end thereof that is closed by a second sealing membrane;

said vial assembly including a first piercing element located between the distal end of said first syringe and said first sealing membrane, said first piercing element being moveable between a retracted position in which said first piercing element is located on a proximal side of said first sealing membrane and an extended position in which said first piercing element pierces said first sealing membrane to provide fluid communication between said first fluid chamber and said first vial; and said vial assembly including a second piercing element located between the distal end of said second syringe and said second sealing membrane, said second piercing element being moveable between a retracted position in which said second piercing element is located on a proximal side of said second sealing membrane and an extended position in which said second piercing element pierces said second sealing membrane to provide fluid communication between said second fluid chamber and said second vial.

11. The sealant delivery system as claimed in claim 10, wherein said syringe assembly further comprises:

a dual barrel plunger including a first plunger rod inserted into a proximal end of said first syringe and a second plunger rod inserted into a proximal end of said second syringe;

a tab interconnecting proximal ends of said first and second plunger rods;

said dual barrel plunger being moveable toward a distal end of said syringe assembly for forcing said first liquid into said first vial for reconstituting said first powdered reactive component to generate a first therapeutic solution and forcing said second liquid into said second vial for reconstituting said second powdered reactive component to generate a second therapeutic solution.

12. The sealant delivery system as claimed in claim 10, wherein said vial housing further comprises:

side-by-side first and second guide channels that extend between proximal and distal ends of said vial assembly housing;

a first proximal projection extending into said first guide channel that is adapted to contact said first piercing element for holding said first piercing element in the retracted position;

a first distal projection extending into said first guide channel that is adapted to contact said first piercing element for holding said first piercing element in the extended position;

a second proximal projection extending into said second guide channel that is adapted to contact said second piercing element for holding said second piercing element in the retracted position;

a second distal projection extending into said second guide channel that is adapted to contact said second piercing element for holding said second piercing element in the extended position.

\* \* \* \* \*